United States Patent
Lauffer et al.

(10) Patent No.: US 7,175,829 B2
(45) Date of Patent: *Feb. 13, 2007

(54) CONTRAST-ENHANCED DIAGNOSTIC IMAGING METHOD FOR MONITORING INTERVENTIONAL THERAPIES

(75) Inventors: Randall B. Lauffer, Brookline, MA (US); Stephen O. Dunham, Madison, NJ (US)

(73) Assignee: Epix Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/961,872

(22) Filed: Oct. 8, 2004

(65) Prior Publication Data

US 2005/0118103 A1   Jun. 2, 2005

Related U.S. Application Data

(63) Continuation of application No. 09/887,706, filed on Sep. 8, 2000, now Pat. No. 6,861,045, which is a continuation of application No. 08/942,989, filed on Oct. 2, 1997, now abandoned.

(51) Int. Cl.
*A61B 5/055* (2006.01)

(52) U.S. Cl. .................. 424/9.364; 424/9.36; 424/9.3; 424/9.1

(58) Field of Classification Search ............... 424/1.11, 424/1.65, 9.1, 9.3, 9.36, 9.361, 9.363, 9.364, 424/9.365

See application file for complete search history.

(56) References Cited

U.S. PATENT DOCUMENTS

| | | | |
|---|---|---|---|
| 5,094,848 A | 3/1992 | Brixner | |
| 5,250,285 A | 10/1993 | Lauffer et al. | |
| 5,649,537 A | 7/1997 | Anelli et al. | |
| 5,828,215 A | 10/1998 | Boettcher | |
| 5,919,967 A | 7/1999 | Amedio et al. | |
| 5,938,599 A | 8/1999 | Rasche et al. | |
| 6,676,929 B2 * | 1/2004 | McMurry et al. | 424/9.364 |
| 6,861,045 B1 * | 3/2005 | Lauffer et al. | 424/9.364 |

FOREIGN PATENT DOCUMENTS

| | | |
|---|---|---|
| CA | 2539215 | 8/1996 |
| WO | WO 95/32741 | 12/1995 |
| WO | WO 96/23526 | 8/1996 |
| WO | WO 97/36619 | 10/1997 |
| WO | WO 98/05625 | 2/1998 |
| WO | WO 00/38738 | 7/2000 |

OTHER PUBLICATIONS

Aime et al., "Yb(III)DOTMA as Contrast Agent in CSI and Temperature Probe in MRS," *Proc. Soc'y Mag. Resn.*, 2:1109, ISSN 1065-9889 (Aug. 19-25, 1995).

Brasch et al., "Assessing Tumor Angiogenesis Using Macromolecular MR Imaging Contrast Media," *J. MRI*, 1997, 7(1):68-74.

Carter et al., "Structure of Serum Albumin," *Adv. Protein Chem.*, 1994, 45:153-203.

Cline et al., "MR Temperature Mapping of Focused Ultrasound Surgery," *Mag. Resn. Med.*, 1994, 31:628-636.

Chu, "The Quantitative Analysis of Structure-Activity Relationships," *Burger's Medicinal Chemistry*, Part 1, pp. 393-418, (4th ed. 1980).

De Poorter et al., "Noninvasive MRI Thermometry with the Proton Resonance Frequency (PRF) Method: In Vivo Results in Human Muscle," *Mag. Resn. Med.*, 1995, 33:74-81.

Dodd et al., "MRI monitoring of the effects of photodynamic therapy on prostate tumours," *Proc. Soc'y Mag. Resn.*, 3:1368, ISSN 1065-9889 (Aug. 19-25, 1995).

Dupas et al., "Delineation of Liver Necrosis Using Double Contrast-Enhanced MRI," *J. MRI*, 1997, 7(3):472-477.

He et al., "Atomic Structure and Chemistry of Human Serum Albumin," *Nature*, 1992, 358:209-215.

Honda et al., "Percutaneous Hot Saline Injection Therapy for Hepatic Tumors: An Alternative to Percutaneous Ethanol Injection Therapy," *Radiology*, 1994, 190:53-57.

Horrocks et al., "Lanthanide Ion Luminescence in Coordination Chemistry and Biochemistry," *Progr. Inorg. Chem.*, 1984, 31:1-104.

Hynynen et al., "The Usefulness of a Contrast Agent and Gradient-Recalled Acquisition in a Steady-State Imaging Sequence for Magnetic Resonance Imaging-Guided Noninvasive Ultrasound Surgery," *Invest. Radiol.*, 1994, 29:897-903.

Hynynen et al., "The feasibility of using MRI to monitor and guide noninvasive ultrasound surgery," *Ultrasound in Med. And Biol.*, 1993, 19(1):91-92.

(Continued)

*Primary Examiner*—Dameron L. Jones
(74) *Attorney, Agent, or Firm*—Fish & Richardson P.C.

(57) ABSTRACT

The present invention relates to a contrast-enhanced diagnostic imaging method for monitoring the efficacy of interventional therapies. The contrast agents useful in this method comprise an image-enhancing moiety (IEM) and a state-dependent tissue binding moiety (SDTBM). These contrast agents exhibit state-dependent binding to one or more components of a targeted tissue or tissue component and provide a detectable change in the signal characteristics of the agent once bound to the targeted tissue. As a result, these agents exhibit a binding affinity for, and thus image contrast of, the targeted tissue which changes as the tissue-state changes during therapy.

6 Claims, 1 Drawing Sheet

OTHER PUBLICATIONS

Kragh-Hansen, "Molecular Aspects of Ligand Binding to Serum Albumin," *Pharm. Rev.*, 1981, 33:17-53.

Lauffer, "Paramagnetic Metal Complexes as Water Proton Relaxation Agents for NMR Imaging: Theory and Design," *Chem. Rev.*, 1987, 87:901-927.

Lauffer et al., "MS-325: A Small-Molecule Vascular Imaging Agent for Magnetic Resonance Imaging," *Acad. Radiol.*, 1996, Supplement 02, 3:S356-358.

Leo et al., "Partition Coefficients and Their Uses," *Chem. Rev.*, 1971, 71:525-616.

Nagel et al., "Contrast-enhanced MR Imaging of Hepatic Lesions Treated with Percutaneous Ethanol Ablation Therapy," *Radiology*, 1993, 189:265-270.

Päuser et al., "Evaluation of Efficient Chemoembolization Mixtures by Magnetic Resonance Imaging Therapy Monitoring: An Experimental Study on the VX2 Tumor in the Rabbit Liver," *Cancer Res.*, 1996, 56:1863-1867.

Poorter et al., "Noninvasive MRI Thermometry with the Proton Resonance Frequency (PRF) Method: In Vivo Results in Human Muscle," *Mag. Resn. Med.*, 1995, 33:74-81.

Rossi et al., "Percutaneous RF Interstitial Thermal Ablation in the Treatment of Hepatic Cancer," *AJR*, 1996, 167:759-768.

Saint-Jalmes, "Precision in Temperature Measurement via $T_1$ or Diffusion Imaging," *Proc. Soc'y Mag. Resn.*, 2:1072, ISSN 1065-9889 (Aug. 19-25, 1995).

Schwarzmaier et al., "Magnetic Resonance Imaging of Microwave Induced Tissue Heating," *Mag. Resn. Med.*, 1995, 33:729-731.

Seibel, "Image-guided minimally invasive therapy," *Surg. Endosc.*, 1997, 11:154-162.

Tracz et al., "Comparison of Magnetic Resonance Images and the Histopathological Findings of Lesions Induced by Interstitial Laser Photocoagulation in the Brain," *Lasers in Surgery and Medicine*, 1993, 13:45-54.

Villringer et al., "Dynamic Imaging with Lanthanide Chelates in Normal Brain: Contrast Due to Magnetic Susceptibility Effects," *Mag. Resn. Med.*, 1988, 6:164-174.

Vogl et al., "Recurrent Nasopharyngeal Tumors: Preliminary Clinical Results with Interventional MR Imaging-controlled Laser-induced Thermotherapy," *Radiology*, 1995, 196:725-733.

Webb et al., "Measurement of microwave induced heating of breast tumors in animal models using cobalt based NMR," *Proc. Soc'y Mag. Resn.*, 1:72, ISSN 1065-9889 (Aug. 19-25, 1995).

Webb et al., "Microencapsulation of fluorine-containing phase transition agents for monitoring temperature changes in-vivo," *Proc. Soc'y Mag. Resn.*, 3:1574, ISSN 1065-9889 (Aug. 6-12, 1994).

\* cited by examiner

CONTRAST-ENHANCED DIAGNOSTIC IMAGING METHOD FOR MONITORING INTERVENTIONAL THERAPIES

CROSS-REFERENCE TO RELATED APPLICATIONS

This application is a continuation application of and claims priority to U.S. application Ser. No. 09/887,706, filed on Sep. 8, 2000, now U.S. Pat. No. 6,861,045, which is a continuation of U.S. application Ser. No. 08/942,989, filed on Oct. 2, 1997, now abandoned, all of which are incorporated in their entirety by reference hereto.

TECHNICAL FIELD OF THE INVENTION

The present invention relates to methods for contrast-enhanced diagnostic imaging. In particular, the present invention relates to methods of MRI and optical imaging which use contrast agents that target a specific tissue or tissue component and permit the monitoring of state changes in the targeted tissue (e.g., denaturation, necrosis, tissue coagulation, apoptosis) that occur during or after interventional therapy. The contrast agents used in this invention exhibit state-dependent binding to one or more components of a targeted tissue and provide a detectable change in the signal characteristics of the tissue-bound contrast agent.

BACKGROUND OF THE INVENTION

Diagnostic imaging techniques, such as magnetic resonance imaging (MRI), x-ray, nuclear radiopharmaceutical imaging, optical (ultraviolet, visible and/or infrared light) imaging, and ultrasound imaging, have been used in medical diagnosis for a number of years. In some cases, the use of contrast media to improve the image quality or to provide specific information has been ongoing for many years. In other cases, such as optical or ultrasound imaging, the introduction of contrast agents is imminent or recent.

MRI and optical imaging methods are unique among imaging modalities in that they yield complex signals that are sensitive to the chemical environment and state of the targeted tissue. While the signal from x-ray or radionuclide agents remains the same whether the agents are free in plasma, bound to proteins, or trapped inside bone, certain agents for MRI and optical imaging will have different signal characteristics in differing physiological environments and pathological states. For example, by binding to tissue components, MRI contrast agents can show changes in the induced relaxation rates or chemical shifts of nearby or attached nuclei. Similarly, an optical dye may exhibit changes in its absorbance, reflectance, fluorescence, phosphorescence, chemiluminescence, scattering, or other spectral properties upon binding.

In general, to provide diagnostic data, the contrast agent must interfere with the wavelength of electromagnetic radiation used in the imaging technique, alter the physical properties of tissue to yield an altered signal, or, as in the case of radiopharmaceuticals, provide the source of radiation itself. Commonly used materials include organic molecules, metal ions, salts or chelates, including metal chelates, particles (particularly iron particles), or labeled peptides, antibodies, proteins, polymers, or liposomes.

After administration, some agents non-specifically diffuse throughout body compartments prior to being metabolized and/or excreted; these agents are generally known as non-specific agents. Alternatively, other agents have a specific affinity for a particular body compartment, cell, cellular component, organ, or tissue; these agents can be referred to as targeted agents.

One application for diagnostic imaging techniques has been in the monitoring of interventional therapies. Common interventional therapies include targeting an undesired tissue or tissue component with high thermal energy using focused ultrasound (e.g., Cline et al., "MR Temperature Mapping of Focused Ultrasound Surgery," *Mag. Resn. Med.*, 31:628–636 (1994)), radiofrequency generators (e.g., Rossi et al., "Percutaneous RF Interstitial Thermal Ablation in the Treatment of Hepatic Cancer," *AJR*, 167:759–768 (1996)), microwave antennae (e.g., Schwarzmaier et al., "Magnetic Resonance Imaging of Microwave Induced Tissue Heating," *Mag. Resn. Med.*, 33:729–731 (1995)), and lasers (e.g., Vogl et al., "Recurrent Nasopharyngeal Tumors: Preliminary Clinical Results with Interventional MR Imaging-Controlled Laser-Induced Thermotherapy," *Radiology*, 196:725–733 (1995)); the use of cryoablation (i.e., liquid nitrogen) and the injection of denaturing liquids (e.g., ethanol, hot saline) directly into the undesired tissue (e.g., Nagel et al., "Contrast-Enhanced MR Imaging of Hepatic Lessions Treated with Percutaneous Ethanol Ablation Therapy," *Radiology*, 189:265–270 (1993) and Honda et al., "Percutaneous Hot Saline Injection Therapy for Hepatic Tumors: An Alternative to Percutaneous Ethanol Injection Therapy," *Radiology*, 190:53–57 (1994)); the injection of chemotherapeutic and/or chaotropic agents into the tissue (e.g., Pauser et al., "Evaluation of Efficient Chemoembolization Mixtures by Magnetic Resonance Imaging of Therapy Monitoring: An Experimental Study on the VX2 Tumor in the Rabbit Liver," *Cancer Res.*, 56:1863–67 (1996)); and photodynamic therapies, wherein a cytotoxic agent is activated in vivo by irradiation with light (e.g., Dodd et al., "MRI Monitoring of the Effects of Photodynamic Therapy on Prostate Tumors," *Proc. Soc'v Mag. Resn.*, 3:1368, ISSN 1065–9889 (Aug. 19–25, 1995)). The shared goal of all such interventional therapies is the treatment of undesirable tissue or tissue component (i.e., cancerous, tumorous, neoplastic tissue or tissue component) by causing the necrosis, ablation, coagulation, or denaturation of such tissue.

To obtain the maximum benefit from such interventional methods, and to minimize side effects (e.g., damage to adjacent tissues), it is essential to monitor, in vivo, the efficacy of the therapy. Indeed, to be truly effective, the interventional therapy must continue until the absolute "death" of the undesired tissue or tissue component (non-viability after removal or conclusion of therapy). Thus, one must not only be able to accurately monitor the progress of the therapy, so as to avoid excessive treatment and possible damage to adjacent tissue, but must also be able to accurately distinguish between truly necrotic tissue and those which may have been injured to a certain extent but remain viable nonetheless.

One way to monitor the efficacy of the interventional therapy is to image the undesired tissue or tissue component during or after such therapy. However, any such diagnostic imaging method must be capable of increasing the contrast between tissues of different pathological states (native vs. denatured, viable vs. necrotic) in such a way to provide two basic classes of information:

1) Detection Data. This includes spectroscopic information necessary to determine the pathologic state of the imaged tissue. The ability to provide this class of information relates to the "specificity" and "sensitivity" of the agent.

2) Feedback and Resolution. These classes of information provide the monitoring of interventional therapeutic procedures that destroy or degrade tissue or tissue components. It is envisioned that with some interventional methods, "real time" feedback (about 1–10 seconds) of the therapy's progress is preferred, while with other methods, a post-therapeutic assessment is adequate. With all interventional therapies, precise spatial resolution (about 1–5 mm) of the tissue treated and any effects on surrounding tissues during treatment is desirable.

Current MRI-based methods for monitoring the efficacy of interventional therapies are generally one of two classes: (1) those that do not use an exogeneous contrast agent but rely on some other observable MR parameter (vide infra); and (2) those that use non-specific, extracellular contrast agents. These methods, however, provide virtually no direct information regarding the pathological state of the tissue or tissue component undergoing interventional therapy (e.g., whether it is native or denatured, necrotic or viable). Further, such methods are largely limited to monitoring thermal ablation therapies and provide limited sensitivity to thermally-induced tissue temperature changes.

Several of these MRI-based methods for monitoring thermal ablation therapies rely on temperature-dependent NMR parameters such as relaxation times ($T_1$ and/or $T_2$), the proton resonance frequency (PRF) of water, phase shifts, and the diffusion coefficient. However, these methods suffer from a number of limitations.

For example, one such method involves monitoring the effect of temperature on the $T_1$ relaxation time of tissue. See, e.g., Cline et al., "MR Temperature Mapping of Focused Ultrasound Surgery," *Mag. Resn. Med.,* 31:628–636 (1994). This approach, however, is inadequate because each tissue has a unique $T_1$ versus temperature profile, and thus, this method requires $T_1$ calibration for each tissue type. The $T_1$ method is also limited in sensitivity, with a tissue dependent change in $T_1$ of only 0.01% to 1.5% per 1° C.

Another method using temperature measurement involves monitoring the effect of temperature on the proton resonance frequency (or chemical shift) of water. This method detects changes in hydrogen bonding and molecular motion of water molecules induced by temperature changes. See, e.g., J. D. Poorter, et al., "Noninvasive MRI Thermometry with the Proton Resonance Frequency (PRF) Method: In Vivo Results in Human Muscle," *Mag. Resn. Med.,* 33:74–81 (1995). However, the low sensitivity of this method (0.01 ppm/° C.) requires the use of high magnetic field strengths (i.e., >4.7 T) which is clinically undesirable. Further, the determination of the chemical shift of water requires absolute stability of the magnetic field and is also highly dependent upon the magnetic susceptibility of the tissue which varies dramatically among different tissue types. Thus, this method, like the $T_1$ method, also requires extensive calibration for each tissue type. Finally, this method does not provide information regarding thermally-induced tissue necrosis or degradation.

Another known method requires monitoring the effect of temperature on the water proton diffusion coefficient. See, e.g., H. Saint Jalmes, "Precision in Temperature Measurement via $T_1$ or Diffusion Imaging," *Proc. Soc'y Mag. Resn.,* 2:1072, ISSN 1065–9889 (Aug. 19–25, 1995). This method, however, is also limited because the diffusion coefficient is sensitive to tissue motion and perfusion.

In all of the above methods, physiologic tissue changes due to increased blood flow, tissue metabolism, or induced edema, can result in unpredictable signal variations (i.e., magnetic susceptibility changes). These effects render standard thermal calibration curves to be of little or no value for the accurate monitoring of thermal ablation therapy. Moreover, measuring temperature alone may be insufficient to accurately determine the efficiency of tissue ablation or side effects on surrounding tissues.

Other methods have also been reported which monitor the effect of temperature on the chemical shift of other magnetic nuclei. For example, the cobalt NMR chemical shift is a very sensitive probe of temperature. However, the low receptivity of $^{59}Co$ requires high field strengths ($\geq 4.7$ T), high concentrations, and extensive measuring times. See A. G. Webb et al., "Measurement of Microwave Induced Heating of Breast Tumors in Animal Models Using Cobalt Based NMR," *Proc. Soc'y Mag. Resn.,* 1:72, ISSN 1065-09889 (Aug. 19–25, 1995). In addition, the toxicity of cobalt agents remains a serious limitation for use in vivo.

Fluorine ($^{19}F$) NMR has also been used to monitor the temperature-dependent phase transitions of liposome-encapsulated fluorocarbons and fluorinated polymers. See, e.g., Webb et al., "Microencapsulation of Fluorine-Containing Phase Transition Agents for Monitoring Temperature Changes in vivo," *Proc. Soc'y Mag. Resn.,* 3:1574, ISSN 1065-9889 (Aug. 6–12, 1994). Clinically, however, $^{19}F$ methods are not useful because of the limited biodistribution of polymeric fluoronated compounds, the chemical shift dependence of fluorinated agents on pH and tissue type, and the need for large magnetic fields. These agents also do not report on thermally-induced tissue necrosis.

Certain contrast agents containing paramagnetic metal complexes have also been suggested to monitor the efficacy of interventional therapies. Such agents can induce large changes in proton chemical shifts (20–40 ppm) of the chelating ligand from the normal range of the water resonance frequency. By paramagnetic shifting of resonances away from the bulk water resonance in vivo, these resonances can be observed. See, e.g., Aime et al., "Yb(III) DOTMA as Contrast Agent in CSI and Temperature Probe in MRS," *Proc. Soc'y Mag. Resn.,* 2:1109, ISSN 1065-9889 (Aug. 19–25, 1995). Although these hyperfine shifted resonances are temperature dependent, they require the use of high concentrations of the paramagnetic complex and clinically impractical, high magnetic fields to detect temperature changes. These complexes also cannot report on thermally-induced tissue necrosis.

More recently, a method for distinguishing between normal and necrotic liver tissue has been described. Dupas et al., "Delineation of Liver Necrosis Using Double Contrast-Enhanced MRI," *J. MRI,* vol. 7, no. 3, pp. 472–77 (1997). This method, however, involves the use of non-specific contrast agents which limits its ability to specifically monitor the state change of the undesired tissue or tissue component. Also, this method requires the administration of multiple contrast agents.

Thus, the known diagnostic imaging methods are limited in that they cannot provide accurate information on the state of the specific tissue or tissue component undergoing interventional therapy (i.e., whether the tissue is in its native or a denatured state, necrotic or viable). Accordingly, there remains a need for a diagnostic imaging method that can non-invasively and accurately monitor the state of a specific tissue or tissue component, which can optionally provide rapid feedback of induced tissue necrosis during interventional therapies.

SUMMARY OF THE INVENTION

The present invention provides a method for contrast-enhanced diagnostic imaging, particularly MRI and optical imaging, of a specific tissue or tissue component that is undergoing or that has undergone interventional therapy. The method comprises the steps of:

(a) administering to a patient a contrast agent capable of binding to a targeted tissue or tissue component that is undergoing or that has undergone interventional therapy;

(b) subjecting the patient to one of MRI, ultraviolet light, visible light or infrared light imaging; and (c) monitoring an imaging signal characteristic of the contrast agent to determine whether the interventional therapy is complete.

The contrast agents used in the present invention comprise an image-enhancing (or signal generating) moiety ("IEM") and a state-dependent tissue binding moiety ("SDTBM"). These contrast agents are capable of demonstrating state-dependent binding to a targeted tissue or tissue component. Such binding leads to a detectable change in the signal characteristics of the contrast agent and thus, permits the determination of state changes within a targeted tissue (e.g., ablation, degradation, or denaturation) that is undergoing or that has undergone interventional therapy.

In one aspect of this invention, the use of the contrast agents allow for "real-time" monitoring during thermal interventional therapy of thermally-induced necrosis. These contrast agents exhibit increased contrast between tissues of different states.

BRIEF DESCRIPTIONS OF THE DRAWINGS

FIG. 2 is a graphical representation of experimental data of the loss in ROI signal intensity over time for MRI images generated using HSA solutions with and without a contrast agent.

FIG. 3 is a graphical representation of experimental data of the effects that changes in ethanol concentration have on the observed relaxivity ($R_1$) for HSA solutions with and without contrast agents.

DETAILED DESCRIPTION OF THE INVENTION

Figure 1:
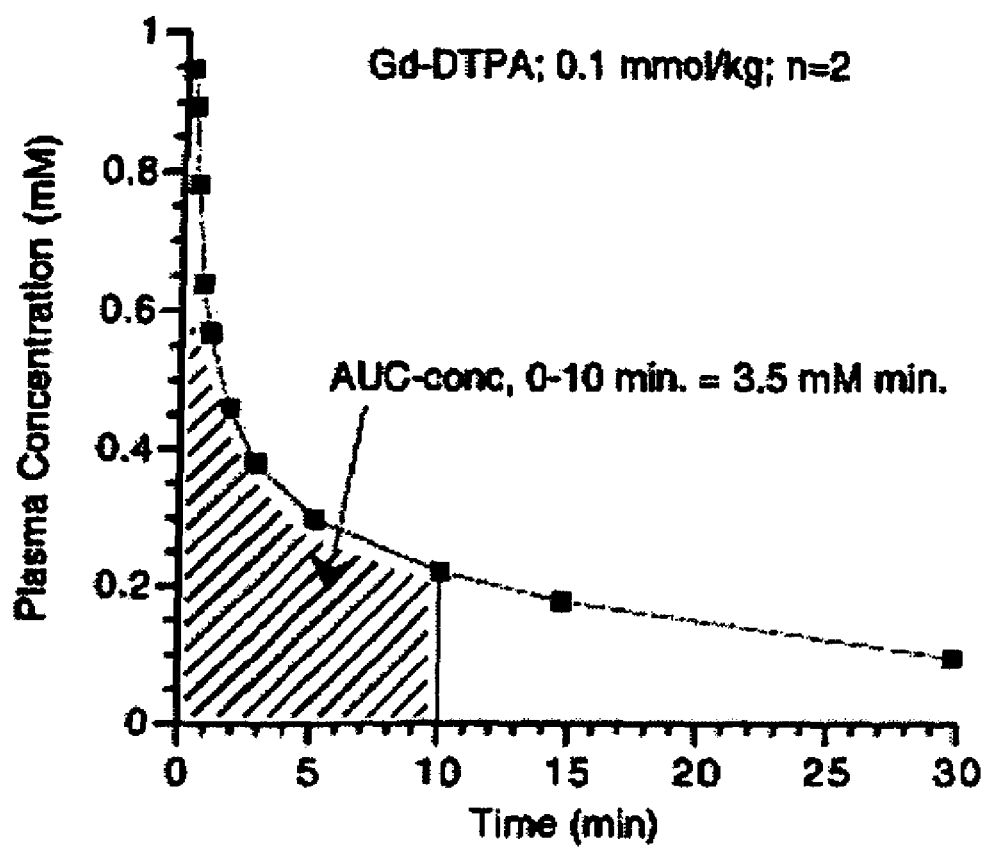
FIG. 1 is a graph demonstrating the Plasma Concentration (mM) of Gd-DTPA over time after tail vein injection in two rats.

In order that the invention herein described may be more fully understood, the following detailed description is set forth.

The present invention provides a non-invasive method for accurately monitoring the efficacy of interventional therapies (i.e., monitoring the state of an undesired tissue or tissue component). In particular, the invention provides a diagnostic imaging method which involves the use of a contrast agent that demonstrates state-dependent binding to a targeted tissue or tissue component and whose signal characteristics are altered when bound to the targeted tissue. The imaging methods useful in this invention are MRI (which includes magnetic resonance spectroscopy techniques) and optical imaging.

As used herein, the term "interventional therapy" refers to any of a number of therapeutic methods where the goal is to induce or to cause the necrosis, ablation or coagulation of some undesired (cancerous, tumorous, neoplastic) tissue or tissue component.

Also, as used herein, the terms "pathological state" or "state" are used herein to broadly describe two physiologic conditions of a tissue or tissue component undergoing interventional therapy. One state can be considered alive, native, or viable. This "initial" state usually describes the tissue before it has undergone any interventional therapy and in which tissue and/or cellular mechanisms such as metabolism and respiration are functional. The "second" state, which describes the tissue during or after it has undergone successful therapy, can be considered nonviable, denatured, necrotic, or apoptotic and in which such tissue and/or cellular mechanisms are aberrant, nonfunctional, or have ceased.

The inventive method herein described comprises the steps of:

(a) administering to a patient a contrast agent capable of binding to a targeted tissue or tissue component that is undergoing or that has undergone interventional therapy;

(b) subjecting the patient to one of MRI, ultraviolet light, visible light or infrared light imaging; and (c) monitoring an imaging signal characteristic of the contrast agent to determine whether the interventional therapy is complete.

The contrast agents used in the present invention comprise an image-enhancing (or signal generating) moiety ("IEM") and a state-dependent tissue binding moiety ("SDTBM"). Because of the combination of these moieties, which are defined in more detail below, the contrast agents are capable of demonstrating state-dependent binding to a targeted tissue or tissue component, and of demonstrating signal characteristics that are altered when bound to the target.

State-dependent binding refers to the relative affinity that the contrast agent demonstrates for the targeted tissue or tissue component which is dependent on the state of the targeted tissue. Thus, the agents used in the present invention have a greater or lesser binding affinity for one or more tissue components in their denatured or necrotic state as compared to the agent's binding affinity for the native or viable tissue.

This state-dependent change in binding results in a localization of the agent to the tissue of one state over the tissue of the other state while at the same time altering the signal characteristics of the agent to enhance detection of the state change that is occurring. For example, if the agent expresses a higher binding affinity for viable or native tissue, where increased binding affinity results in a more intense signal, then the viable tissue is imaged (or detected) as a "hot spot." During the course of interventional therapy, this hot spot would become "cool" as the viable tissue became necrotic, because of the reduced binding affinity of the agent for the necrotic tissue. Conversely, if the agent expresses a higher binding affinity for necrotic or nonviable tissue then that tissue would develop as a hot spot during the course of the therapy.

It is preferred that the state-dependent binding affinity of the agent exhibit high sensitivity to the physiological state change. The preferred agents are those that have a binding affinity and corresponding signal changes that is sensitively tuned to correspond to the state change that the tissue or tissue component is undergoing. In one aspect of the invention, by monitoring the change in signal during the course of the interventional therapeutic procedure, sensitive real-time monitoring of the efficacy and extent of tissue ablation is enhanced.

Structure of the Contrast Agents

The contrast agents used in the present invention must comprise at a minimum an image-enhancing (or signal-generating) moiety ("IEM"), and a state-dependent tissue binding moiety ("SDTBM"). A physiologically compatible linking group ("L") may optionally be used to attach the IEM to the SDTBM. Examples of suitable linking groups include linear, branched, or cyclic alkyl, alkyl, aryl, ether, polyhydroxyl, polyether, polyamine, heterocyclic, peptide, peptoid, phosphate, sulphate, or other physiologically compatible covalent linkages. The linking group can provide important physicochemical stability to the complex by enhancing the halflife in blood or other biological fluids and compartments. The linking group can also provide a means for biodegradation and subsequent excretion of the agent.

1. Image Enhancing Moiety (IEM)

The first domain of the contrast agents used in the present invention is an IEM which can be any chemical or substance used to provide the signal or contrast in imaging. The IEM must be capable of generating a different signal characteristic when the agent is bound to a tissue or tissue component as compared to that of the free agent. For optical imaging, this can be a change in absorbance, reflectance, fluorescence, scattering, phosphorescence, chemiluminescence, an increase or decrease in the number of absorbance peaks or any change in their wavelength maxima, or any other change which by external detection would correspond to a bound IEM. For MRI, this can be a change in the induced relaxation rates of water protons ($1/T_1$ or $1/T_2$) or any other nearby nuclei, or a shift of one or more peaks in the NMR spectrum of either the IEM or peaks that appear from nuclei in the binding site for the SDTBM.

Accordingly, the IEM can be an organic molecule, metal ion, salt or chelate, including metal chelates; a metal cluster or particle (particularly iron particle); or a labeled peptide, protein, polymer or liposome. For optical imaging (which uses ultraviolet, visible or infrared light), the IEM can also be any organic or inorganic dye. Examples of useful organic dyes include indocyanine green and fluoroscein. Examples of inorganic dyes include luminescent metal complexes, such as those of Eu(III), Tb(III) and other lanthanide ions (atomic numbers 57–71). See W. Dew. Horrocks & M. Albin, Progr. Inorg. Chem. 1984, 31, pp. 1–104.

A particularly useful IEM is a physiologically compatible metal chelate compound consisting of one or more cyclic or acyclic organic chelating agents complexed to one or more metal ions. For optical imaging, the preferred metal ions include those with atomic numbers 13, 21–31, 39–42, 44–50, or 57–83. For MRI, the preferred metal ions include those with atomic numbers 21–29, 42, 44, or 57–83, and more preferably a paramagnetic form of a metal ion with atomic numbers 21–29, 42, 44, or 57–83. Where the IEM comprises a paramagnetic metal chelate, the preferred paramagnetic metal is selected from the group consisting of Gd(III), Fe(III), Mn(II and III), Cr(III), Cu(II), Dy(III), Tb(III and IV), Ho(III), Er(III), Pr(III) and Eu(II and III). The most preferred is Gd(III).

If the IEM is a metal chelate, it must not dissociate to any significant degree while the agent passes through the body, including the targeted tissue. Significant release of free metal ions, and in particular free paramagnetic metal ions, can result in toxicity, which would only be acceptable in pathological tissues.

In general, the degree of toxicity of a metal chelate is related to its degree of dissociation in vivo before excretion. Toxicity generally increases with the amount of free metal ion. For complexes in which kinetic lability is high, a high thermodynamic stability (a formation constant of at least $10^{15}$ M$^{-1}$ and more preferably at least $10^{20}$ M$^{-1}$) is desirable to minimize dissociation and its attendant toxicity. For complexes in which kinetic lability is comparatively lower, dissociation can be minimized with a lower formation constant, i.e., $10^{10}$ M$^{-1}$ or higher.

Toxicity is also a function of the number of open coordination sites in the complex. In general, fewer water coordination sites lowers the tendency for the chelating agent to release the paramagnetic metal. Preferably, therefore, the complex contains two, one, or zero open coordination sites. The presence of more than two open sites in general will unacceptably increase toxicity by release of the metal ion in vivo.

In order to effectively enhance MRI images, the complex must be capable of enhancing the relaxation rates $1/T_1$ (longitudinal, or spin-lattice) and/or $1/T_2$ (transverse, or spin-spin) of water protons or other imaging or spectroscopic nuclei, including protons, P-31, C-13, Na-23, or F-19 on the IEM, other biomolecules, or injected biomarkers. Relaxivities $R_1$ and $R_2$ are defined as the ability to increase $1/T_1$ or $1/T_2$, respectively, per mM of metal ion (i.e., mM$^{-1}$s$^{-1}$). For the most common form of clinical MRI, water proton MRI, relaxivity is optimal where the paramagnetic ion bound to the chelating ligand still has one or more open coordination sites for water exchange (R. B. Lauffer, Chemical Reviews, 87, pp. 901–927 (1987)). However, this must be balanced with the stability of the metal chelate (vide infra) which generally decreases with increasing numbers of open coordination sites. More preferably, therefore, the complex contains only one or two open coordination sites.

The type of chelating ligand can greatly affect the water exchange rate for a MRI agent. In particular, the water exchange rate can play a significant role in the tissue contrast generated in thermal ablation therapies. In general, a higher water exchange rate gives a higher $R_1$ because of the greater number of water molecules interacting with the paramagnetic center; conversely, a lower exchange rate gives a lower $R_1$. Thus, a metal chelate complex that has a slow water exchange rate (kex-298K=500–10,000 ns) will generally show an increase in $1/T_1$ ($R_1$) as the temperature increases, reflecting the positive effects of increased thermal motion of water molecules and increased water exchange near the paramagnetic center; $R_1$ then usually reaches a maximum contrast value at temperatures higher than physiological. At some temperature, the contrast will then drop off to minimal values, as the beneficial effect of increased water exchange is offset by the insufficient amount of time each water molecule spends near the paramagnetic center.

A metal chelate with a moderately fast water exchange rate (kex-298K 10–100 ns) will demonstrate a relatively flat dependence of $1/T_1$ ($R_1$) on temperature, which will then drop off at some higher temperature, again because of the insufficient amount of time each water molecule spends near the paramagnetic metal in such conditions.

A metal chelate with a very fast water exchange rate (kex-298K 0.1–10 ns) at physiologic and higher temperatures will demonstrate a decreasing $1/T_1$, as the increased thermal motion of the water molecules further limits the time each water molecule spends near the paramagnetic center. However, such a chelate will demonstrate an increase in $1/T_1$ at lower temperatures (i.e. cryogenic) due to the increased time each water molecule spends in the vicinity of the paramagnetic metal.

When the method of the present invention is used to monitor thermal ablation therapies, it is preferred that chelates of moderately fast water exchange be used as the IEM, in order to maximize the contrast between the initial native or viable tissue state ($R_1$initial) and the denatured or necrotic tissue state ($R_1$second). For those therapies using cryogenic techniques, it may be preferable to employ chelates of very fast water exchange rates, in order to take selective advantage of the increase in $1/T_1$ ($R_1$) as the temperature is lowered. In all methods of interventional therapy, it is preferred that the sensitivity of the $R_1$ profile with respect to tissue state coincide precisely with the denaturation profile of the tissue or tissue component of interest.

In addition to increasing the $1/T_1$ or $1/T_2$ of tissue nuclei via dipole-dipole interactions, MRI agents can affect two other magnetic properties and thus be of use clinically:

1) an iron particle or metal chelate of high magnetic susceptibility, particularly chelates of Dy, Gd, or Ho, can alter the MRI signal intensity of tissue by creating microscopic magnetic susceptibility gradients (A. Villringer et al, Magn. Reson. Med. 6, pp. 164–174 (1988)). No open coordination sites on a chelate are required for this application.

2) an iron particle or metal chelate can also be used to shift the resonance frequency of water protons or other imaging or spectroscopic nuclei, including protons, P-31, C-13, Na-23, or F-19 on the injected agent or the tissue component to which it binds. Here, depending on the nucleus and strategy used, zero to three open coordination sites may be employed.

The organic chelating ligand should be physiologically compatible. The molecular size of the chelating ligand should be compatible with the size of the paramagnetic metal. Thus Gd(III), which has a crystal ionic radius of 0.938A, requires a larger chelating ligand than iron (III), which has a crystal ionic radius of 0.64 A.

Many suitable chelating ligands for MRI agents are known in the art. These can also be used for metal chelates for other forms of biological imaging. Preferred IEMs include:

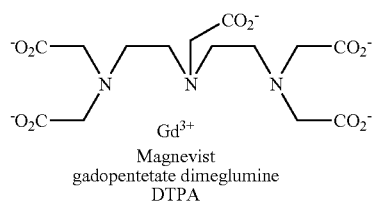

Magnevist
gadopentetate dimeglumine
DTPA

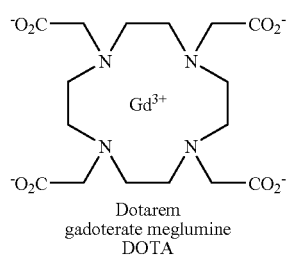

Dotarem
gadoterate meglumine
DOTA

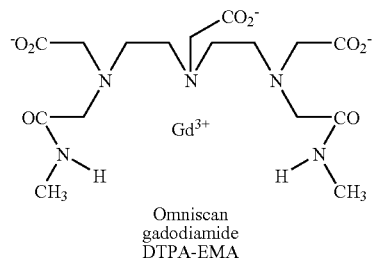

Omniscan
gadodiamide
DTPA-EMA

-continued

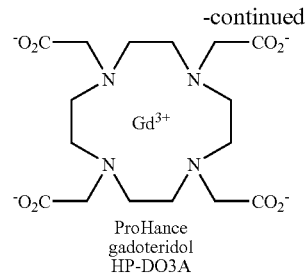

ProHance
gadoteridol
HP-DO3A

It is known in the art that other metals may be substituted for $Gd^{3+}$ in certain applications.

2. State-Dependent Tissue Binding Moiety (SDTBM)

The second domain of the contrast agents used in this invention is a state-dependent tissue binding moiety (SDTBM) which provides the targeting functionality to the agent. The SDTBM can be highly variable, depending on the application of interest. Thus, the specific structure of the SDTBM will depend on the specific tissue or tissue component to be bound. Generally, however, the SDTBM must furnish the contrast agent with a state-dependent change in binding affinity for the targeted tissue or tissue component. This state-dependent change in binding affinity must also result in a detectable change in the signal characteristics of the contrast agent. The change in binding affinity should be sufficiently sensitive and the number of binding sites sufficiently large such that contrast is generated when the state of the tissue changes.

The SDTBM may comprise a small-molecule or, alternatively, a biomolecule. Biomolecules can vary in molecular weight and size, but all share the same fundamental feature in that they are biologically derived or synthesized from naturally occurring subunits (i.e., amino acids or nucleotides). Examples of biomolecules include receptor ligands, saccharides, lipids, hormones, peptides, proteins, nucleotides and nucleic acids (DNA, RNA), and antibodies including fragments thereof and monoclonal and genetically engineered versions.

Small-molecules, on the other hand, are well known synthetically derived, organic molecules of relatively low molecular weight having little or no chemical similarity to biomolecules. Small-molecules do not typically include biomolecule subunits and linkages (e.g., natural amino acids linked by amide bonds). Examples of small-molecules include synthetic drugs, lipophilic or amphiphilic organic molecules, and porphyrins.

More preferred SDTBMs are those that bind reversibly to proteins in plasma, interstitial space (the fluid between cells), or intracellular space. While any biomolecule or small-molecule that binds to a protein could be used, most useful are those that bind to proteins which either exist in high concentration or have a large number of binding sites for certain ligands. Since the native state of many proteins in tissues, plasma, or interstitial or intracellular space is usually more well-defined structurally and chemically than the denatured or unfolded state, it is a preferred aspect of the invention to design the SDTBM to bind with higher affinity to such native states than to the corresponding denatured states. This difference in binding affinity between the native and denatured states leads to a detectable change in the signal characteristics of the agent.

A quantitative measurement of the ability of a contrast agent to relax water protons, and consequently affect the MRI image, is provided by its relaxivity. As described earlier, relaxivity is the dependence of water proton signal intensity upon the concentration of paramagnetic metal ion in solution. Relaxivity is defined as the induced $T_1$ or $T_2$ relaxation per unit time ($R_1$ or $R_2$ in units of mM-1 sec-1) observed for a contrast agent, where the concentration of the agent is expressed in millimolar (mM).

The physical properties of a gadolinium complex affect the relaxivity of a contrast agent. The number of water molecules bound to the gadolinium complex, the rate of exchange of the water molecule with bulk solution, the relaxation time of the seven unpaired electrons, and the rotational tumbling time (known as the rotational correlation time) of the contrast agent in solution all contribute to the overall observed relaxivity. Alteration in these physical properties can dramatically alter the relaxivity. The effect of water exchange rate on relaxivity has been discussed earlier. In addition, the binding of small, relatively low molecular-weight gadolinium chelates to large macromolecules slows the rotation tumbling time and increases the relaxation enhancement by factors of 3 to 10. Binding of the contrast agent to the protein causes the magnetic fluctuations between the paramagnetic ion and the water protons to occur on the same time scale as the Larmor frequency, generating the most efficient longitudinal ($T_1$) relaxation possible and the highest possible relaxivity. Thus state-dependent binding of MRI contrast agents to large macromolecules, such as proteins, is an efficient way to increase the MRI signal (and contrast) in one state over the other. Image contrast is generated between areas which have different levels of binding to the contrast agent. In a preferred aspect of the invention, image contrast is generated between areas of high binding affinity (the native state) and low binding affinity (the denatured state).

To generate contrast between tissues or tissue components of different state, it is desired to have the contrast agent binding affinity change by at least 20% or more when the tissue changes state. For example, if the agent was 90% bound (i.e., 10% free) to the viable state of a target tissue or tissue component (i.e. HSA), the agent should be 72% bound or less under the same conditions to the nonviable (e.g., denatured) state. Greater contrast will be generated if the difference in binding affinity is higher. It is desirable that the binding affinity of the contrast agent for the second tissue state (that resulting from or during interventional therapy) should be 80% or less of the binding affinity for the first tissue state as compared to the binding affinity in the second state, preferably 50% or less, more preferably 30% or less, even more preferably 20% or less, and most preferably 10% or less.

In the case where the IEM is an appropriate chromophore for use in optical imaging, the invention requires that there be a measurable difference between the optical properties of the non-tissue bound drug and the tissue-bound contrast agent. For example, the maximal absorbance of indocyanine green is shifted from 770–780 nm to 790–805 nm upon binding in plasma or blood. This state-dependent binding can be used to detect tissue denaturation by monitoring the shift in absorbance of the dye as the tissue is denatured and the protein no longer binds. Those of skill in the art will appreciate that the optical agents useful in this invention will in general tend to provide higher sensitivity to tissue state. Therefore, to generate sufficient contrast, the optical agents may not require as large a binding affinity difference or as large a signal difference between the two tissue states as the MR agents of the present invention.

The state-dependent binding must also result in a characteristic signal change of the contrast agent. In MRI, this state-dependent signal change can be manifested as a change in the induced relaxation rates ($1/T_1$ or $1/T_2$) of water protons, or relaxivities $R_1$ and $R_2$. In a preferred aspect of the present invention, the relaxivity of the agent in the second tissue state ($R_1$second) is desirably 80% or less of the relaxivity ($R_1$initial) of the agent in the initial tissue state. Preferably $R_1$second is 50% or less of the $R_1$initial, more preferably 20% or less, and even more preferably 10% or less.

It is also prefered that after the interventional therapy is complete and the targeted tissue is returned to physiological conditions (e.g., in the case of thermal denaturation, after the temperature is returned to physiological temperature), the $R_1$ relaxivity of the agent is still lower than the relaxivity of the agent in the initial tissue state ($R_1$initial), preferably 80% or less of the $R_1$initial, more preferably 50% or less of the $R_1$initial, even more preferably 20% or less, and most preferably 10% or less. It is also desirable that the $R_1$ relaxivity of the contrast agent, after the interventional therapy is complete and the targeted tissue is returned to physiological conditions, be maintained at the relaxivity of the agent measured immediately after the interventional therapy is complete.

As previously indicated, the specific structure of the SDTBM will depend on the specific tissue or tissue component to be bound. Accordingly, it is necessary to first determine which tissue or tissue component is to be targeted.

A number of possible binding sites are contemplated. Such binding sites include nucleic acids, glycosaminoglycans (formerly known as acid mucopolysaccharides), calcified tissue, bone, fat, synovial fluid, cell membranes, proteins, lipoproteins, enzymes, proteoglycans, amyloids and ceroids. The preferred binding sites are proteins, with serum and structural/connective proteins being more preferred.

Where the target is a protein, suitable proteins include human serum albumin (HSA, 0.7 mM in plasma; lower concentrations in interstitial space); fatty acid binding protein (FABP, also known as Z-protein or protein A, roughly 0.1 mM in the primary cells of the liver, kidney, heart and other tissues); glutathione-S-transferase (GST, also known as ligandin; roughly 0.1 mM in the primary cells of the liver, kidney, heart and other tissues); alpha 1-acid glycoprotein (AAG, MW 41000, 0.55g–1.4g/L), as well as lipoproteins (for example, those concentrated in atherosclerotic plaque). Other examples include the structural proteins of the extracellular matrix (collagens, laminin, elastin, fibronectin, entactin, vitronectin), amyloid (including the beta-2 amyloid protein (A4) of Alzheimer's disease), ceroid (or lipofuscin), and glycoproteins (for example, osteonectin, tenascin, and thrombospondin).

A preferred protein target for positively charged contrast agents or contrast agents containing basic SDTBMs would be alpha 1-acid glycoprotein (AAG). The plasma levels of this positive acute phase protein varies significantly with disease state. For example, the concentrations of AAG increase two to four fold following inflammatory stimuli and plasma levels of AAG have been suggested as a prognostic aid for glioma, metastatic breast and other carcinoma, neonatal infection, and chronic pain. Elevated levels have been noted in atherosclerosis, Chron's disease, myocardial infarction, nephritis, and bacterial, viral, and post-operative infections. The highly soluble AAG has a single polypeptide chain of 183 amino acids and is characterized by several unusual properties, including a high carbohydrate and sialic acid content (45% and 12%, respectively) and a low isoelectric point of pH 2.7. Alpha 1-acid glycoprotein has been implicated in binding of numerous basic drugs, including propranolol (Ka=11.3×10$^5$), imipramine (Ka=2.4×10$^5$), and chloropromazine (Ka=35.4×10$^5$). The percentage of free lignocaine has been correlated with the concentration of AAG in patients (0.4 to 3 gl$^{-1}$), implying that selective binding to AAG over other proteins (e.g., HSA) in plasma could be achieved using rational drug design methods.

Ligands for HSA, FABP, and GST are more preferred SDTBMs since these are negatively charged molecules or tend to be neutral with partial negatively charged groups (e.g., an ester, amide, or ketone carbonyl oxygen); such compounds are, in general, thought to be less toxic than positively charged molecules. Of these three proteins, HSA may be most preferred in some cases, since ligands for FABP and GST would require some intracellular uptake before binding. Generally, intracellular uptake is avoided for contrast agents (except in the liver) to minimize toxicity. HSA is present in substantial quantities in many extracellular fluid environments including plasma, the interstitial space of normal and cancerous tissues, synovial fluid, cerebral spinal fluid, and inflammatory or abscess fluid. In many pathologic tissues such as tumors, inflammation, atherosclerotic plaque, or the walls of atherosclerotic arteries, capillaries are leaky, resulting in even higher HSA levels. This can enhance the utility of the agents of this invention since a large number of interventional therapies target diseased tissues.

HSA is also preferred because it is known to have good affinity and high capacity for binding a wide variety of structurally dissimilar molecules usually at a large number of binding sites. Thus, more flexibility exists in the design of the contrast agents.

For binding to the native state of HSA, a wide range of hydrophobic or amphiphilic substances may be useful as the SDTBM (U. Kragh-Hansen, Pharm. Rev., 33, pp. 17–53 (1981); X. M. He et al., Nature, 358, pp. 209–215 (1992); D. C. Carter, Adv. Protein Chem., 45, pp. 153–203 (1994)). These include but are not limited to small-molecules comprising at least one aliphatic, alkoxy, alkylthio, alkylcarbonyl, alkylcarbonyloxy, aryl or heterocyclic group with 1 to 60 carbon atoms and, optionally, one or more nitrogen, oxygen, sulfur, halogen, aliphatic amide, ester sulfonamide, acyl, sulfonate, phosphate, hydroxyl or organometallic substituents. Alternatively, but less preferred, the SDTBM may be a biomolecule such as a peptide containing hydrophobic amino acid residues and/or substituents with or without hydrophobic or hydrophilic termination groups.

As stated above, for binding to HSA, a wide range of hydrophobic substances may be useful as the SDTBM. In general, binding affinity to HSA and possibly other proteins will increase with the hydrophobicity of the SDTBM. Theoretical estimates of the hydrophobicity of a substituent such as a SDTBM can be obtained by calculating the contribution to the log of the octanol-water (or octanol-buffer) partition coefficient (log P) for the TBM itself using the Hansch 1 constant for substituents. See A. Leo and C. Hansch, "Partition Coefficients and their Uses," Chemical Reviews, 71, pp. E525–616 (1971); K. C. Chu, "The Quantitative Analysis of Structure-Activity Relationships," Burger's Medicinal Chemistry, Part 1, pp. 393–418, (4th ed. 1980). Binding affinity will increase with increasing log P contributions. For example, for substituents on aliphatic groups, the following 1 constants can be used:

| Group | 1-aliphatic |
|---|---|
| CH$_3$ | 0.50 |
| Phenyl | 2.15 |

For substituents on aryl groups, the following constants can be used:

| Group | 1-aliphatic |
|---|---|
| CH$_3$ | 0.56 |
| CH$_2$CH$_3$ | 1.02 |
| Phenyl | 1.96 |

Thus, the log P contribution for a p-methylbenzyl group attached to an IEM would be calculated as follows (using the value of the 1-aliphatic for CH$_3$ as an estimate for the —CH$_2$— group):

log $P$ contribution=0.50+2.15+0.56=3.2

In binding to HSA, a minimum log P contribution of 2 (equivalent to 4 CH$_3$ groups or one phenyl ring) is required to achieve significant binding. More preferred is a log P contribution of 3. Even more preferred is a log P contribution of 4.

HSA binding can be assessed by equilibrium dialysis or ultrafiltration using 4.5% weight/volume HSA in a pH 7.4 buffer. Preferably at least 10%, and more preferably at least 50%, more preferably at least 80%, and most preferably at least 95% of the contrast agent is bound to the native state of HSA at a physiological relevant concentrations (0.01–10 mM in plasma for MRI and optical imaging). In this application, the measurement of percent binding of the contrast agent to HSA has an error of approximately +/−5%. Protein binding to other proteins or to serum can be assessed in a similar fashion.

The addition of lipophilic groups into a contrast agent is likely to decrease the solubility of the agent. To retain efficient solubility of the contrast agent at clinically effective dosage levels or higher, it may be preferred to incorporate one or more hydrogen-bonding groups (oxygen, nitrogens, etc.) into the SDTBM.

While purely aliphatic groups can be used as SDTBMs, these may not be as preferred as mixed aliphatic-aryl groups or purely aryl groups. Especially when a negative charge is attached to a purely aliphatic groups, particularly long and flexible ones, the contrast agent may interfere with the metabolism of endogenous molecules such as fatty acids or the interactions between membrane proteins and lipids. This may increase the toxicity of the agent. Thus it is preferred that the SDTBM contain at least one aryl ring.

In the case of native-state HSA-bound MRI agents for tumor or tissue enhancement, it is especially preferable for the contrast agent to contain two or more distinct lipophilic groups to fully immobilize the agent when bound to the protein. These groups may be on one SDTBM, or as two or more separate chemical groups attached to the contrast agent. Because of their bulky nature and rigidity, it is preferable that the two or more groups each consist of an aromatic ring, with the two or more rings in the entire molecule arranged in a rigid, non-planar orientation.

The magnetic efficiency, or relaxivity, of an MRI agent is generally highest when the agent has a rotational correlation time approximately equal to HSA (R. B. Lauffer, Chemical Reviews, 87, pp. 901–927 (1987)). While a small-molecule such as Gd-DTPA has a rotational correlation time of approximately 0.1 nanoseconds (nsec), HSA has a correlation time of greater than 5–10 nsec; if a chelate has this longer correlation time, the magnetic fluctuations between the paramagnetic ion and the water protons occur on the same time scale as the Larmor frequency, generating the most efficient longitudinal (T$_1$) relaxation possible and thus the highest possible relaxivity. Any flexibility of the chelate when bound to the protein is expected to decrease the effective rotational correlation time and thus decrease relaxivity. Since one site of attachment to the protein may still yield flexibility in several directions, additional sites of attachment may be preferred.

As previously indicated, the state-dependent binding must also result in a characteristic signal change of the contrast agent. In MRI, this state-dependent signal change can be manifested as a change in the induced relaxation rates ($1/T_1$ or $1/T_2$) of water protons, or relaxivities $R_1$ and $R_2$. Thus, where HSA is the target, the degree to which an agent has been tuned for maximum relaxivity can be assessed by measuring the state-dependent relaxivity-bound ($R_1$-bound) in the presence of HSA in its two physiological states: native and denatured. In a preferred aspect of the present invention, the relaxivity of the agent in the second tissue state ($R_1$second) is desirably 80% or less of the relaxivity ($R_1$initial) of the agent in the initial tissue state. Preferably $R_1$second is 50% or less of the $R_1$initial, more preferably 20% or less, and most preferably 10% or less.

This requires measuring the relaxivity of the free chelate ($R_1$-free) as well as the relaxivity ($R_1$-observed) and percent binding of the agent in 4.5% HSA at its two physiologic states. In a preferred aspect of the invention, $R_1$-free corresponds to $R_1$ observed in the denatured state. The $R_1$-observed is a mole fraction weighted average of $R_1$-free and $R_1$-bound:

$$R_1\text{-observed} = (\text{fraction-free} * R_1\text{-free}) + (\text{fraction-bound} * R_1\text{-bound})$$

Thus:

$$R_1 - \text{bound} = \frac{[R_1 - \text{observed} - (\text{fraction-free} * R_1 - \text{free})]}{\text{fraction-bound}}$$

State-Dependent Binding To HSA

As indicated above, the preferred targeted protein for the contrast agents to be used in this invention is HSA. For such an application, it is desirable that the contrast agent exhibit enhanced blood half-life to increase the extent to which the agent remains in the blood (i.e., bound to HSA) and thus, available throughout the course of the interventional therapy. Extended blood half-life may be achieved by including a linking group (L) which functions as a blood half-life extending moiety ("BHEM") to reduce the rate of hepatocyte uptake of the contrast agent. See U.S. patent application Ser. No. 08/382,317, filed Feb. 1, 1995, which is incorporated by reference. The BHEMs are extremely hydrophilic groups which can hydrogen-bond with water. The presence on a contrast agent of the hydrophilic BHEM reduces the hepatocyte uptake of the agent.

Examples of chemical groups which would serve as a BHEM include carbon, phosphorous, tungsten, molybdenum, or sulfur atoms having attached charged or neutral heteroatoms such as oxygen, nitrogen, sulfur or halogens (especially fluorine) possessing two or more lone electron pairs (i.e., full or partial negative charge) or electropositive hydrogen atoms (i.e., protonated amine) for hydrogen bonding with water. These include groups such as sulfone, ether, urea, thio-urea, amine sulfonamide, carbamate, peptide, ester, carbonate and acetals. Preferred groups include those which possess one or more partial or full negative charges in aqueous solution at physiological pH wherein the negatively charged atoms cannot be partially or fully neutralized by covalent or coordinate covalent bonding to the IEM. Examples of these preferred BHEMs include negatively charged groups such as phosphate mono-ester, phosphate diester, carboxylate, and sulphonate. More preferred are those which have phosphate groups or any ester forms thereof. Even more preferred are phosphate diesters, since: a) they are highly hydrophilic with four hydrogen-bonding oxygens; b) they are relatively readily synthesized using techniques shown below; c) they serve as excellent linkers between the IEM and the SDTBM; and d) because phosphate compounds exist and are metabolized naturally in the body, phosphate diester-containing contrast agents are expected to be non-toxic.

The incorporation into a contrast agent of this invention of a BHEM results in prolonged blood retention of the agent. Blood retention is preferably measured by calculating, in a rat plasma pharmacokinetic experiment, the area under the plasma concentration versus time curve ("Area Under the Curve" or "AUC-conc.") for a specific length of time (e.g., 0–10 minutes, 0–30 min., 0–60 min., 0–120 min., or 0-infinity). Blood retention (as measured by AUC-conc) can be evaluated experimentally by administration of a contrast agent to rats, rabbits, or higher mammals. It has been observed that blood half-life extension is greater in rabbits and higher mammals than in rats. In this application, blood half-life data, as measured by AUC-conc., represents experimentation in rats. The error associated with this data is approximately +/±10%.

The reason that a half-life measurement itself is not used is that the mathematical definition of this quantity is often not clear and the resulting estimates are variable depending on the pharmacokinetic model used and the length of time the blood samples were obtained.

For example, the average plasma concentrations observed after tail vein injection of 0.1 mmol/kg of $Gd^{153}$-labeled Gd-DTPA in two rats is shown in FIG. 1. Using the Macintosh program KaleidaGraph, this AUC-conc. from 0 to 10 minutes was calculated as 3.5 mM min.

The contrast agents of this invention, useful in targeting serum proteins such as HSA, exhibit an AUC-conc. increase of at least 20% when the BHEM is added to the IEM and SDTBM. They preferably exhibit an AUC-conc. increase of at least 40%, more preferably at least 70% and even more preferably at least 100%. In general, the increase in AUC-conc. caused by a BHEM is greater when the binding in plasma is significant, e.g., 20%–50% or greater. The calculated percent increase in AUC-conc. may be different for AUC-conc.'s determined over different time periods. Generally, the percent increase in AUC-conc. caused by the BHEM is greater for AUC-conc.'s taken over longer periods, e.g, 0–30 min., rather than 0–10 min.

Since the structure and physical characteristics of the entire contrast agent molecule will govern its binding in plasma, it is important to select IEMs and BHEMs that are compatible with the desired binding. For example, to achieve binding to the positively charged binding sites on HSA, it is preferred to have IEMs and BHEMs of net neutral or net negative charge to reduce the possibility of repulsion and perhaps even increase binding affinity. For binding to alpha acid glycoprotein, at least some portion of the contrast agent should be positively charged. For binding to globulins, at least some portion of the contrast agent should be steroidal in nature. For binding to lipoproteins, at least some portion of the contrast agent should be lipophilic or fatty acid-like.

It is contemplated that the BHEM may be arranged in a variety of positions with respect to the IEM and SDTBM. However, the position of the moieties may not be such that one moiety interferes with the intended function of the other. For example, in an HSA-binding contrast agent the placement of the BHEM should not block the ability of the STDBM to bind the agent to HSA. Since the major binding sites in HSA are sock-like (X. M. He et al., *Nature*, 358, pp. 209–215 (1992); D.C. Carter, *Adv. Protein Chem.*, 45, pp.

153–203 (–1994)), with hydrophobic interiors (especially near the "toe" region) and positively charged "ankle" regions, the binding affinity of a STDBM would decrease if the distal portion of the STDBM were made extremely hydrophilic. As an illustrative example, if the STDBM is a phenyl ring, the most preferred BHEM position on the ring is ortho, followed by meta. A hydrophilic group in the para position would reduce the STDBM's binding affinity to HSA.

For IEMs that consist of a metal chelate, it is preferred that the BHEMs and SDTBMs not be attached to the IEM so as to significantly reduce the strength of the binding between the metal ion and chelating ligand. For example, where the chelating arm is acetate, the BHEM or SDTBM is preferably not attached to the acetate oxygen.

Another positional requirement is that the BHEM's negatively charged atoms cannot be partially or fully neutralized by covalent or coordinate covalent bonding to the IEM; this ensures that in aqueous systems the very hydrophilic atoms of the BHEM will be highly solvated. For example, when the IEM is a metal chelate, it is important to position the negatively charged atoms of the BHEM so that they cannot become neutralized by the positively charged metal ion ($M^{n+}$) of the IEM through coordinate covalent bonding via the formation of 5- or 6-membered chelate rings, the most stable ring sizes. Since 5-membered chelate rings are the most stable for the metal ions of interest for IEMs (such as gadolinium), it is most important to prevent their formation. Thus, as shown in the drawing below, a phosphinate ($—PO_2—$) or phosphonate ($—PO_3—$) BHEM cannot be attached to the nitrogen atom of an aminocarboxylate chelating agent via a $—CH_2—$ linker since this will form a very stable 5-membered chelate ring. Similarly, a phosphodiester ($—OPO_3—$) BHEM should not be attached to the nitrogen atom of an aminocarboxylate chelating agent via a $—CH_2—$ linker since this could form a 6-membered chelate ring. However, both of these BHEMs can be attached to other positions, such as the ethylene backbone of the ligand. In some cases, as shown, it may be preferred to increase the length of the linker group to make certain that 5- or 6-membered rings cannot form.

Phosphinate BHEM

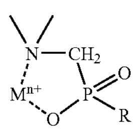

Strongly disfavored (5-membered chelate ring, charge neutralized)

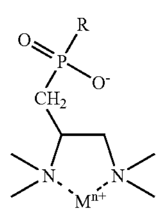

Disfavored (6-membered chelate ring, charge neutralized)

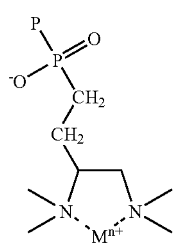

More preferred (no possibility of 5- or 6-membered chelate rings or charge neutralization)

It is contemplated that the moieties of this invention can be positioned in the contrast agent so that the following structures may result:

$$IEM—[(L)_m—\{(BHEM)_s—(SDTBM)_o\}_p]_q \quad (1)$$

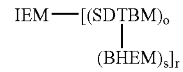

(2)

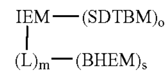

(3)

wherein m can be equal to 0–4, s, o, and p can be the same or different and equal to 1–4, and r and q are at least one.

If the moieties of this invention are positioned in the contrast agent as in structure (1) above, the BHEM is preferably sulfone, urea, thio-urea, amine, sulfonamide, carbamate, peptide, ester, carbonate, acetals and more preferably 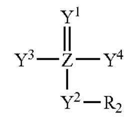 or ester forms, where Z=P, W, Mo, or S $Y^1$, $Y^2$=O or S $Y^3$, $Y^4$=O, S or not present $R_2$=H, $C_{1-6}$ alkyl or not present.

Most preferably, the BHEM is a phosphate group.

If the moieties of this invention are positioned in the contrast agent as in structure (2) above, the BHEM is preferably sulfone, urea, thio-urea, amine, sulfonamide, carbamate, peptide, ester, carbonate, acetals and more preferably the BHEM has the following formula:

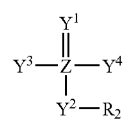

or ester forms, where Z=P, W, or Mo $Y^1$, $Y^2$=O or S $Y^3$, $Y^4$=O, S or not present $R_2$=H, $C_{1-6}$ alkyl or not present.

Most preferably, BHEM is a phosphate group.

If the moieties of this invention are positioned in the contrast agent as in structure (3) above, the BHEM is preferably $SO_3^-$ or ester forms, sulfone, urea, thio-urea, amine, sulfonamie, carbamate, peptide, ester, carbonate, acetal and more preferably 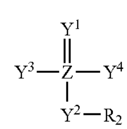 or ester forms, where Z=P, W, Mo, or S $Y^1$, $Y^2$=O or S $Y^3$, $Y^4$=O, S or not present.

$R_2$=H, $C_{1-6}$ alkyl or not present.

Most preferably, the BHEM is a phosphate group.

It is contemplated that if the moieties of this invention are positioned in the contrast agent as in structure (3) above, preferred contrast agents have the formulas:

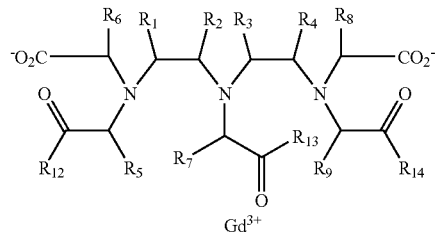

or

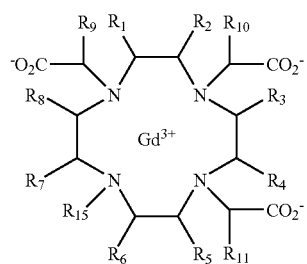

where $R_1$, $R_2$, $R_3$, $R_4$, $R_5$, $R_6$, $R_7$, $R_{10}$, $R_9$, $R_{10}$, $R_{11}$ and $R_{16}$ can be the same or different and selected from the group consisting of H, SDTBM, BHEM and $C_{1-6}$ alkyl, provided that at least one of these Rs is SDTBM and at least another is BHEM, $R_{12}$, $R_{13}$ and $R_{14}$ can be the same or different and selected from the group consisting of $O^-$ and $N(H)R_{17}$, $R_{15}$=H, $CH_2CH(OH)CH_3$, hydroxy alkyl or $CH(R_{16'})COR_{12}$ and $R_{17}$=H or $C_{1-6}$ alkyl.

For contrast agents comprising the formulas shown above, the BHEM is preferably sulfone, ether, urea, thio-urea, amine, amide, sulfonamie, carbamate, peptide, ester, carbonate, acetal and more preferably $COO^-$ or ester forms, $SO_3^-$ or ester forms and

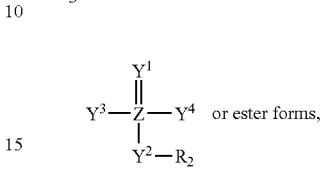

or ester forms, where Z=P, W, Mo, or S $Y^1$, $Y^2$=O or S $Y^3$, $Y^4$=O, S or not present.

$R_2$=H, $C_{1-6}$ alkyl or not present.

In the case of an HSA-binding contrast agent, the BHEM may be placed in between the IEM and the SDTBM as shown above in structure (1) or on the IEM away from the SDTBM as shown above in structure (3). In this manner the full binding potential of the hydrophobic SDTBM group can be expressed without interference from the hydrophilic BHEM group.

Contrast agents useful in the present invention that exhibit state-dependent binding to HSA are set forth in U.S. patent application Ser. No. 08/382,317, filed Feb. 1, 1995. For example, the following agents are useful:

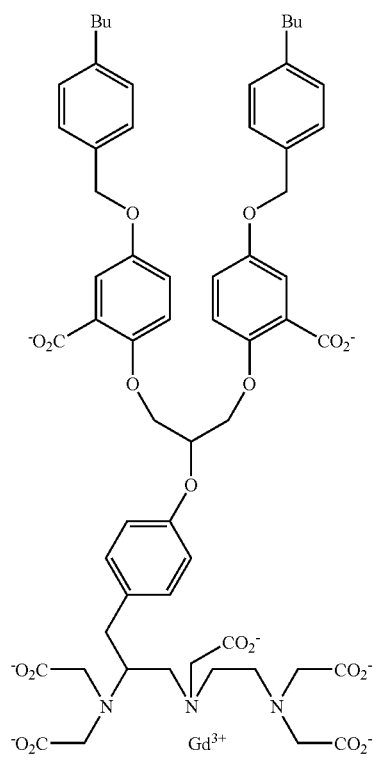
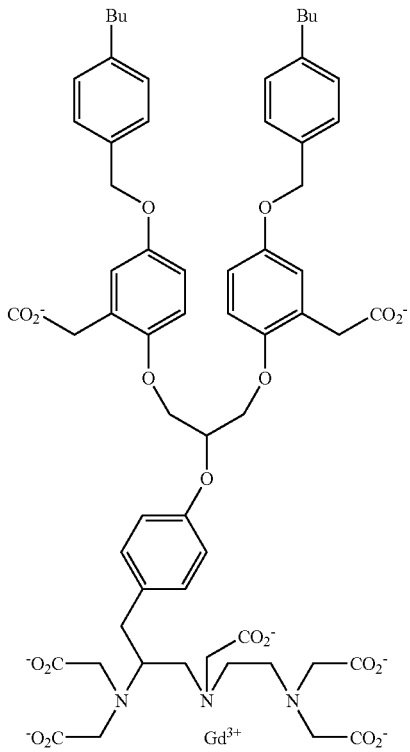

-continued
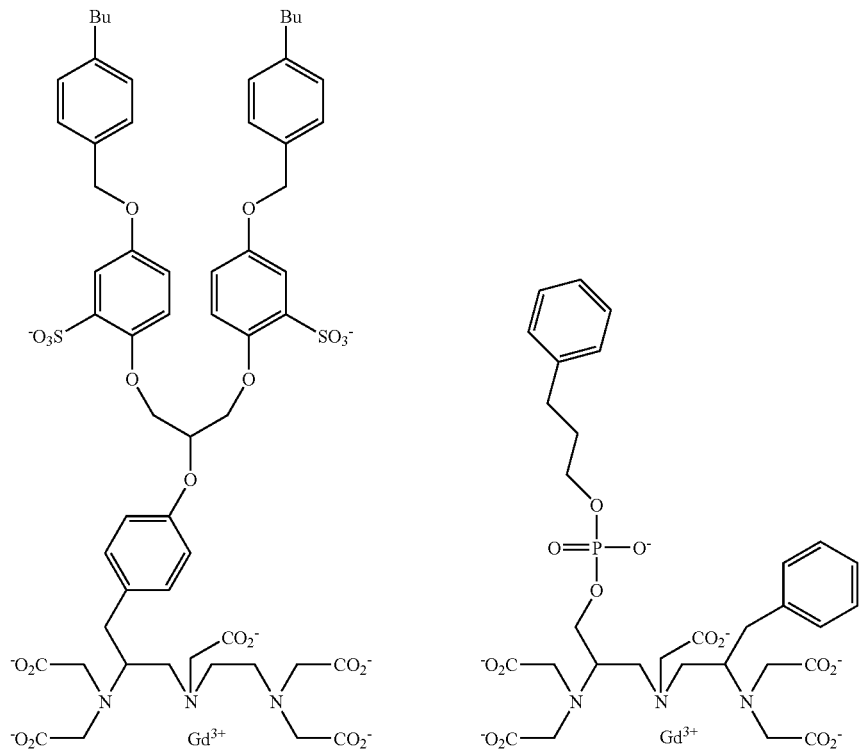
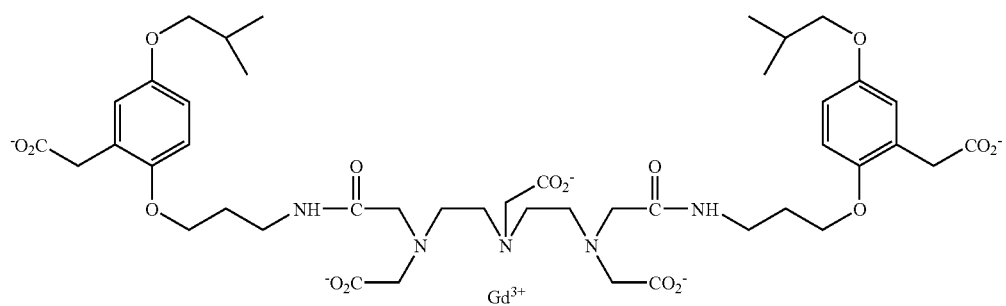
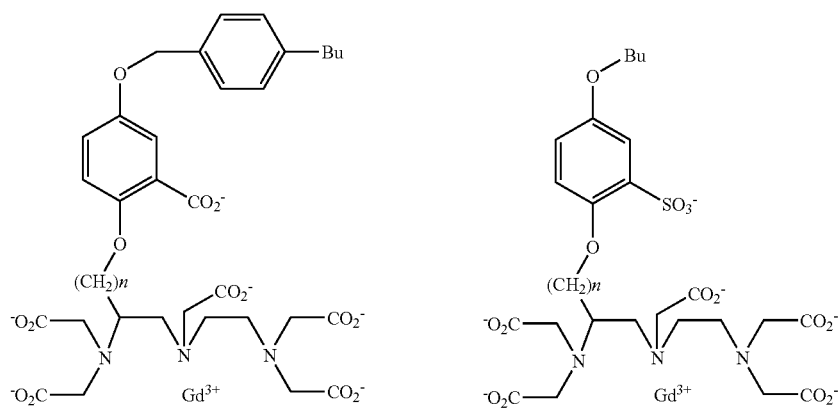

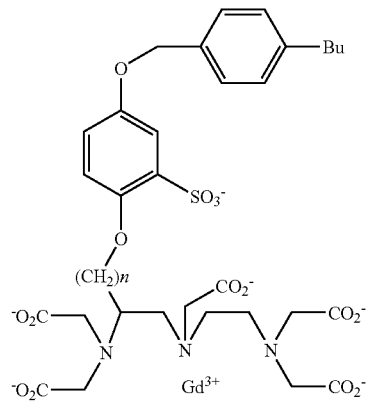
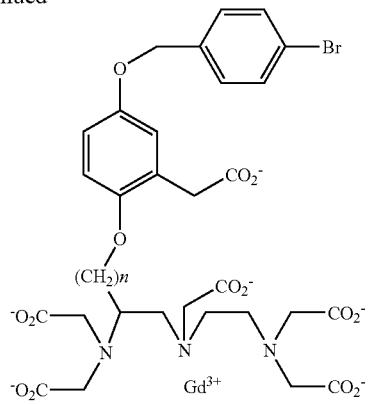
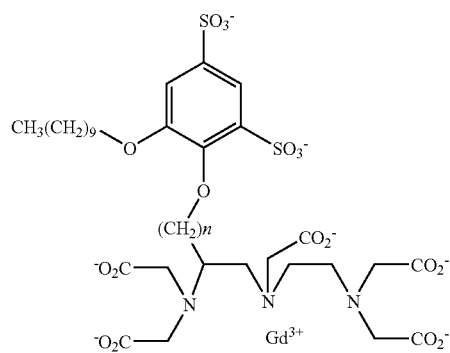
wherein n can be equal to 1–4.
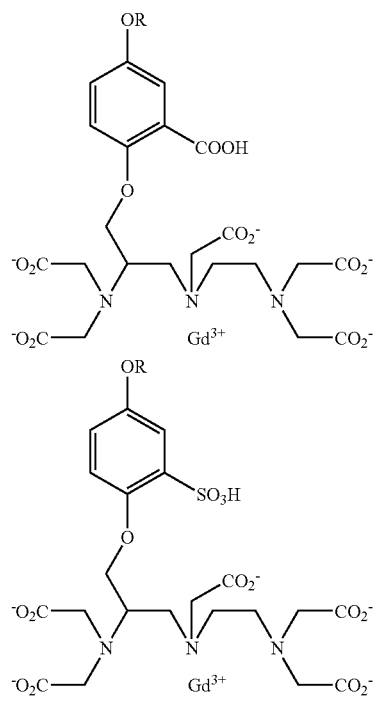
wherein R comprises an aliphatic group and/or at least one aryl ring, or comprises a peptide containing hydrophobic amino acid residues and/or substituents with or without hydrophobic or hydrophilic termination groups.
The preferred contrast agents useful in this invention are:
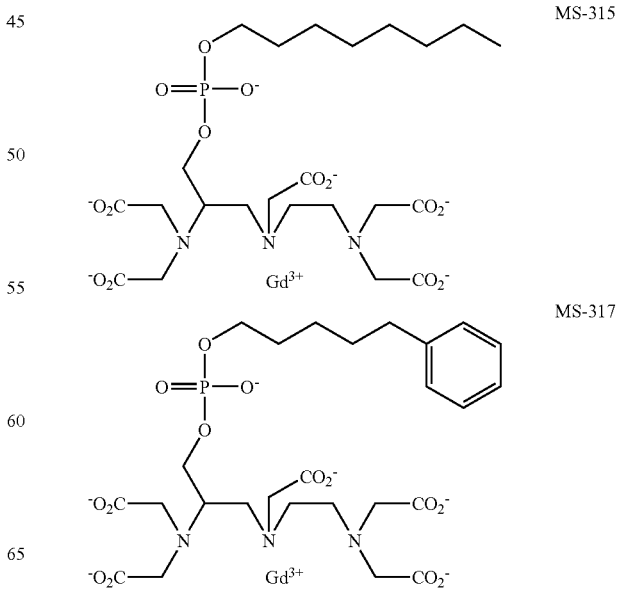

-continued

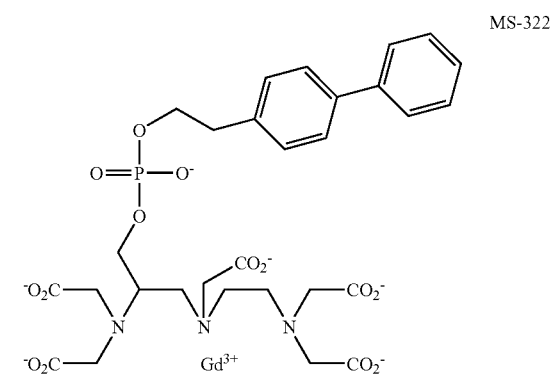
MS-322

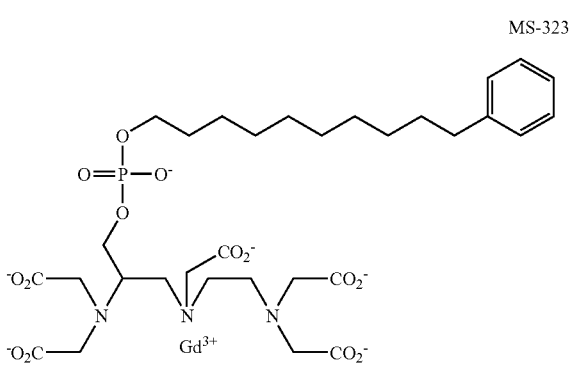
MS-323

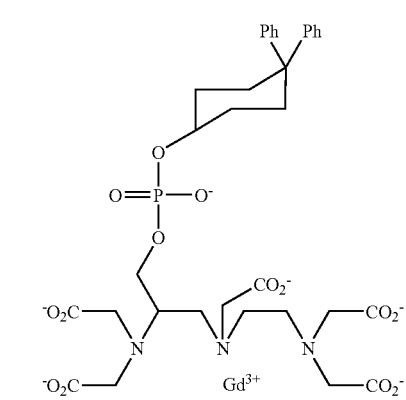
MS-325

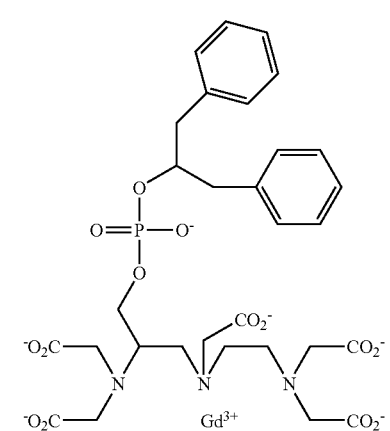
MS-326

-continued

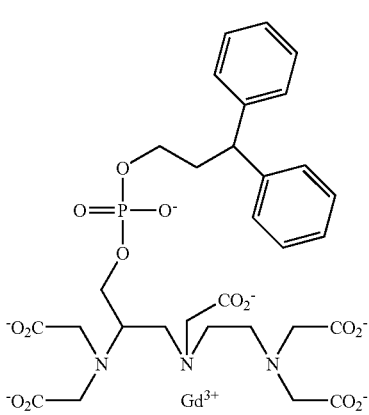
MS-327

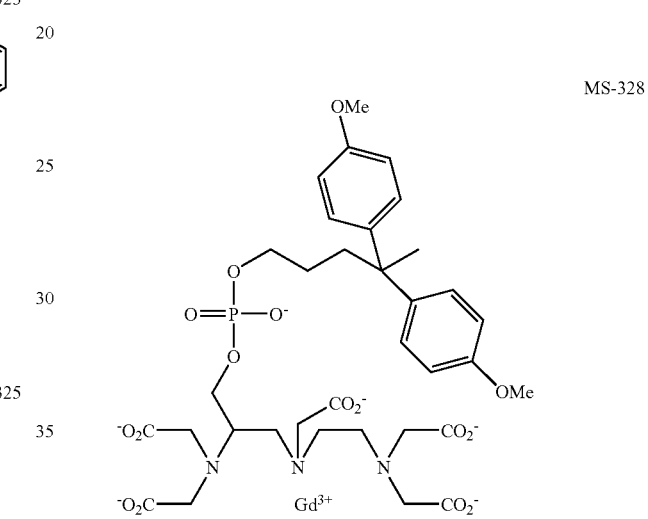
MS-328

The more preferred contrast agents with state-dependent binding to HSA are MS-317, MS-322, MS-325 and MS-328. The most preferred is MS-325.

Use of the Contrast Agents

The agents used in this invention are defined to include pharmaceutically acceptable derivatives thereof. A pharmaceutically acceptable derivative means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system).

It is also contemplated that the agents used in this invention may comprise a pharmaceutically acceptable salt. Pharmaceutically acceptable salts of this invention include those derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium, magnesium and zinc salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained. The preferred salts of this invention are the N-methyl-D-glucamine, calcium and sodium salts.

The pharmaceutical compositions of this invention comprise any of the complexes of the present invention, or pharmaceutically acceptable salts thereof, together with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, TRIS (tris (hydroxymethyl)amino-methane), partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

Since the contrast agents of this invention may bind to plasma proteins, in some cases depending on the dose and rate of injection, the binding sites on plasma proteins may become saturated. This will lead to decreased binding of the agent and could compromise half-life or tolerability. Thus, it may be desirable to inject the agent pre-bound to a sterile albumin or plasma replacement solution. Alternatively, an apparatus/syringe can be used that contains the contrast agent and mixes it with blood drawn up into the syringe; this is then re-injected into the patient.

The compounds and pharmaceutical compositions of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term "parenteral" as used herein includes subcutaneous, intravenous, intramuscular, intra-articular, intra-synovial, intrasternal, intrathecal, intrahepatic, intralesional and intracranial injection or infusion techniques.

When administered orally, the pharmaceutical compositions of this invention may be administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, when administered in the form of suppositories for rectal administration, the pharmaceutical compositions of this invention may be prepared by mixing the agent with a suitable non-irritating excipient which is solid at room temperature but liquid at rectal temperature and therefore will melt in the rectum to release the drug. Such materials include cocoa butter, beeswax and polyethyleneglycols.

As noted before, the pharmaceutical compositions of this invention may also be administered topically, especially when the target of treatment includes areas or organs readily accessible by topical application, including the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

For administration by nasal aerosol or inhalation, the pharmaceutical compositions of this invention are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosage depends on the sensitivity of the diagnostic imaging instrumentation, as well as the composition of the contrast agent. For example, for MRI imaging, a contrast agent containing a highly paramagnetic substance, e.g., gadolinium (III), generally requires a lower dosage than a contrast agent containing a paramagnetic substance with a lower magnetic moment, e.g., iron (III). Preferably, dosage will be in the range of about 0.001 to 1 mmol/kg body weight per day of the active metal-ligand complex. More preferably, dosage will be in the range of about 0.005 and about 0.05 mmol/kg body weight per day.

In the case were optical imaging is used to monitor the interventional therapy, the doses of the agent will be approximately equal to that in MRI (0.001–10 mmol/kg). Also, as with MRI contrast agents, the administration of optical agents is well known in the art.

It should be understood, however, that a specific dosage regimen for any particular patient will also depend upon a variety of factors, including the age, body weight, general health, sex, diet, time of administration, rate of excretion, drug combination, and the judgment of the treating physician.

Following administration of the appropriate dosage of the contrast agent, the patient is then subjected to either MRI or optical imaging (ultraviolet light, visible light or infrared light imaging). The appropriate settings and imaging parameters to carry out these imaging techniques, as well as data collection and analysis (i.e., monitoring the agent's signal characteristics) are well known or involve commonly accepted principles.

The final step of the method of this invention is to monitor an imaging signal characteristic of the administered contrast agent. For optical imaging, such signal characteristics include absorbance, reflectance, fluorescence or phosphorescence and/or their lifetimes, chemiluminescence, scattering, or other spectral properties. For MRI imaging, such signal characteristics include the $R_1$ and $R_2$ relaxivities ($1/T_1$ and $1/T_2$, respectively).

In a more preferred aspect of this invention, "real-time" monitoring is possible where an image is generated and thus the signal characteristic is monitored periodically throughout the course of the interventional therapy. The frequency in which the images are generated and monitored will depend on the type and duration of the therapy.

In order that this invention may be more fully understood, the following examples are set forth. These examples are for the purposes of illustration only and are not to be construed as limiting the scope of the invention in any way.

EXAMPLES

The following is a synthetic scheme for the preferred contrast agents useful in the method of invention, and in particular for that of MS-325. See U.S. patent application Ser. No. 08/833,745, filed Apr. 11, 1997 and incorporated herein by reference. Another useful, although not as preferred, synthetic scheme for these contrast agents is described in U.S. patent application Ser. No. 08/382,317, filed Feb. 1, 1995 and incorporated herein by reference.

First, an alcohol ROH is reacted with $PCl_3$, preferably at a molar ratio of 1:1, to form a dichlorophosphine reaction product (I):

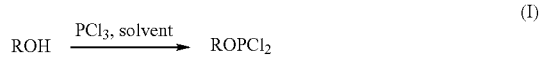

The R group may be a linear, branched, or cyclic aliphatic, aryl, heterocyclic, peptidic, peptoid, deoxyribo- or ribo-nucleotidic or nucleosidic, or cyclic or acyclic organic chelating agent group, which may optionally be substituted with one or more nitrogen, oxygen, sulfur, halogen, aliphatic, amide, ester, sulfonamide, aryl, acyl, sulfonate, phosphate, hydroxyl, or organometallic substituents.

This reaction takes place in the presence of an ethereal or hydrocarbon solvent and is carried out at a temperature of from about −50° C. to about 15° C., preferably from about −10° C. to about −5° C., for a period of from about 30 minutes to about 3 hours, preferably from about 1 to about 1.5 hours. The solvent may be any ethereal or hydrocarbon solvent and preferably, may be selected from the group consisting of heptanes, methyl-t-butyl ethers, dioxanes, tetrahydrofurans, diethyl ethers, and ethylene glycol dialkyl ethers. More preferably, the solvent is tetrahydro The dichlorophosphine (I) is then reacted with from about 5 to about 6 equivalents of an amine base to form a bis(amino)phosphino reaction product (II):

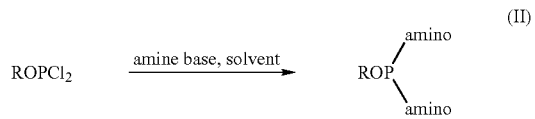

This reaction also takes place in the presence of an ethereal or hydrocarbon solvent, as described above, and is carried out at a temperature of from about −50° C. to about 15° C., preferably from about −10° C. to about −5° C., for a period of from about 30 minutes to about 3 hours, preferably from about 15 to about 30 minutes. The base used to form reaction product (II) may be any amine base, preferably a base having a pKa value of from about 5 to about 11, and more preferably selected from the group consisting of imidazole, 2,4-dimethylimidazole, 1H-tetrazole, dialkylamines (methyl, ethyl, butyl), pyridine, piperazine, piperidine, pyrrole, 1H-1, 2, 3-triazole, and 1,2,4-triazole. In a more preferred embodiment, the base is imidazole.

The bis(amino)phosphino compound (II) is then reacted with from about 0.75 to about 1.0 equivalents of a second alcohol $R^1OH$, where $R^1$ may be any of the substituents defined above for the R group, to form an (amino)phosphino reaction product (III):

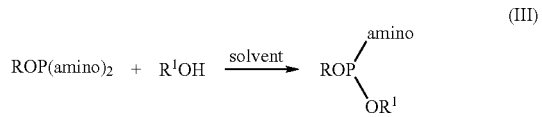

This reaction takes place in the presence of an ethereal or hydrocarbon solvent and carried out at a temperature of from about −50° C. to about 15° C., preferably from about −10° C. to about −5° C., for a period of from about 30 minutes to about 3 hours, preferably from about 1.0 to about 1.5 hours.

The solvent may be any ethereal or hydrocarbon solvent and preferably may be selected from the group consisting of heptanes, methyl-t-butyl ethers, dioxanes, tetrahydrofurans, 1,3-dioxolanes, diglymes, diethyl ethers, dialkyl ethers, and ethylene glycol dialkyl ethers. More preferably, the solvent is tetrahydrofuran.

Finally, the (amino)phosphino compound (III) is reacted with about one equivalent of acidic water, preferably having a pH of about 2.5 to about 5, and about 1 or more equivalents of an oxidant to form the desired phosphodiester compound (IV):

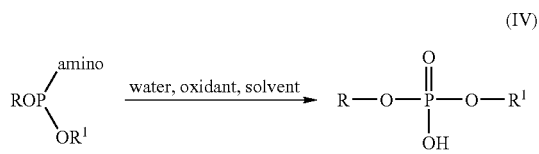

The oxidant may be any peroxide type oxidant and preferably selected from the group consisting of periodates. More preferably, the oxidant is sodium periodate.

The above hydrolysis and oxidation is carried out in a solvent mixture at a temperature of from about −15° C. to about 25° C., preferably from about 0° C. to about 2° C., for a period of from about 10 to about 24 hours, preferably from about 10 to about 15 hours. The solvent mixture comprises any combination of solvents selected from the group consisting of ethereal or hydrocarbon solvents. Preferably, the solvent mixture comprises tetrahydrofuran, heptane and toluene in the volume ratio of 10:10:1.

In accordance with this synthetic scheme, the chelating ligand in the MS-325 complex is prepared as follows.

Preparation of [(4,4-diphenylcyclohexyl)phospho-oxymethyl]diethylene triaminepenta-acetic acid The preparation of the chelating ligand used in the MS-325 complex is shown below in Scheme I:

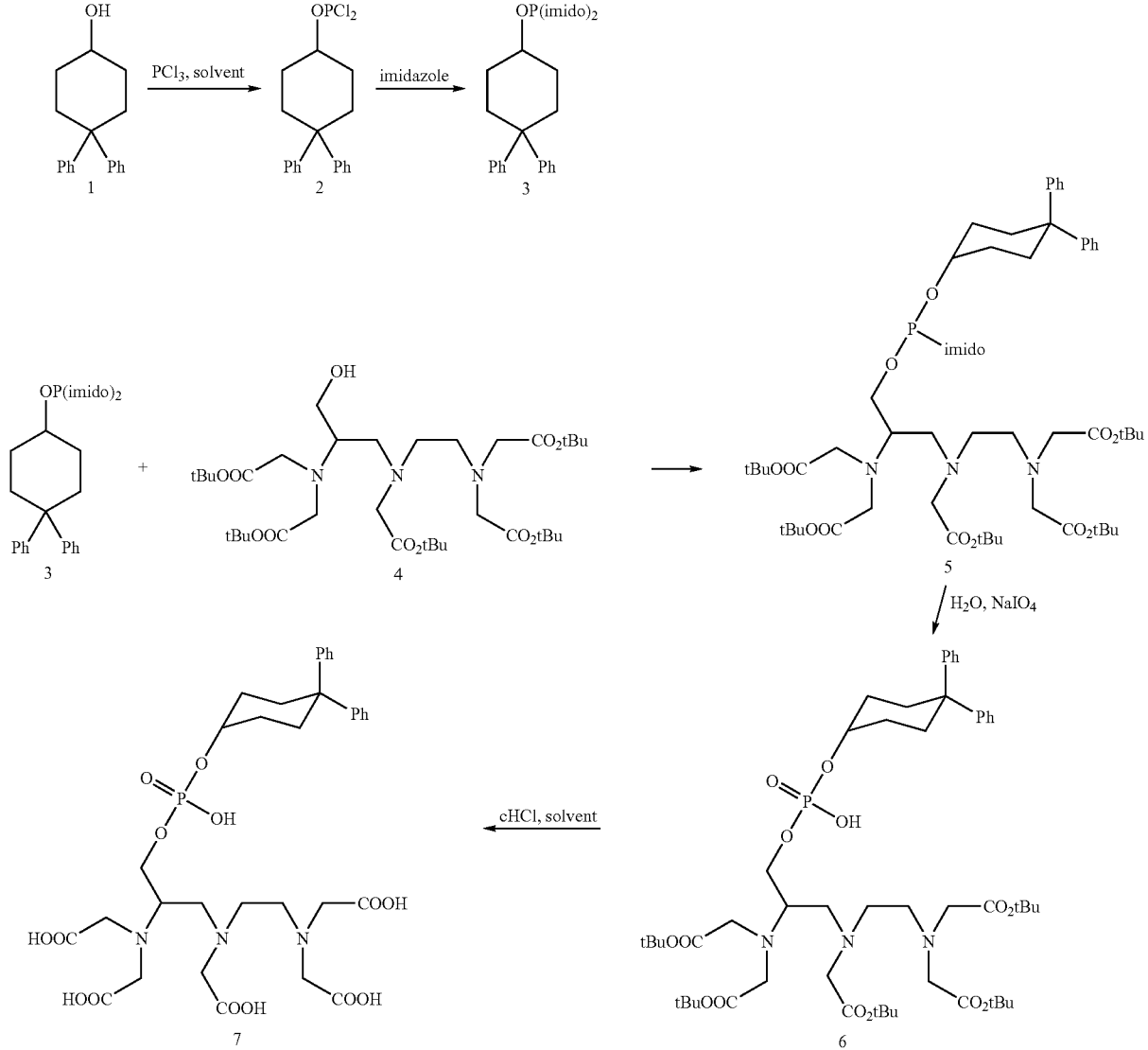

In a single reaction vessel that contained a solution of phosphorous trichloride (13.2 mL, 0.151 mol) in tetrahydrofuran (202 ml) was added a solution of 4,4-diphenylcyclohexanol (1) (38.34 g, 0.152 mol) in tetrahydrofuran (243 ml) while stirring and maintaining an internal temperature of −6.2° C. to −5.3° C. for 1.5 hours. The mixture was then stirred for an additional 34 minutes yielding a dichlorophosphine reaction product (2), having a $^{31}$P NMR chemical shift of 174.28 ppm.

To this solution, imidazole (51.34 g, 0.753 mol) in tetrahydrofuran (243 ml) was added while stirring and maintaining an internal temperature of −7.8° C. to −3.6° C. for 37 minutes. The resulting mixture was then stirred for an additional 20 minutes yielding a solution of a bis(amino) phosphino reaction product (3) having a $^{31}$P NMR chemical shift of 106.36 ppm.

To this mixture was added a solution consisting of 2-(R)-hydroxymethyldiethylenetriamine pentaacetic acid, penta-t-butyl ester (4) (160.0 g, 0.128 mol, purity: 56.32% by weight) in heptane (114 ml) while stirring and maintaining an internal temperature of −6.8° C. to −4.8° C. for 1 hour and 6 minutes. This mixture was then stirred for an additional 23 minutes yielding a solution (5) having a $^{31}$P NMR chemical shift of 123.8 ppm.

Finally, water (202 ml) was added over a period of about 1 minute while maintaining an internal temperature of −6.5° C. to 6.5° C. The mixture was stirred for 5 minutes followed by the addition of heptane (620 ml), toluene (70 ml) and 5N aqueous hydrochloric acid (202 ml) over 5 minutes while maintaining an internal temperature of 1.0° C. to 12.1° C. Sodium periodate (22.6 g, 0.106 mol) was then added over a period of 3 minutes while maintaining an internal temperature of 10.5° C. The reaction mixture was warmed to room temperature over 35 minutes and stirred an additional 2.5 hours yielding a solution (6) with a $^{31}$P NMR chemical shift of 4.27 ppm. The layers were separated and the organic layer was washed with 10% aqueous sodium thiosulfate (2×809 mL).

To the above organic layer was added tetraoctylammonium bromide (8.21 g, 0.015 mol). Concentrated hydrochloric acid (11.51 M, 405 mL) was then added over a period of 22 minutes while maintaining an internal temperature of 22.8° C. to 25.0° C. This mixture was stirred for 16.0 hours yielding a compound (7) with a $^{31}$P NMR chemical shift of 7.78 ppm. The layers were separated and the organic layer discarded.

To the above aqueous layer was added 8M aqueous sodium hydroxide (630 mL) until a pH of 6.56 was recorded. The solution was concentrated under reduced pressure (50° C. to 55° C., vacuum 85 mm Hg) until 400 mL of solvent was collected (approximately 1 hour). The solution was cooled to room temperature and amberlite XAD-4 resin (92.0 g) was added. The suspension was stirred for 50 minutes at room temperature and filtered to give a light yellow aqueous solution (1.1 L).

The above solution was loaded onto C-18 reversed phase silica gel (271 g, packed wet in methanol and then washed with 800 mL methanol, 800 mL methanol/water, 1:1 and 800 mL water) and eluted with water. The first 1.0 L of eluent collected was discarded and the next 1.3 L collected were retained. To the retained solution was added 6N aqueous hydrochloric acid (60 mL to a pH=2.15) and 3N aqueous hydrochloric acid (30 mL to a pH=1.63). The slurry was stirred for 1.25 hours and filtered. The solid was washed with pH 1.67 aqueous solution (500 mL) and dried (48–50° C., 4–6 mm Hg) to a constant weight (18.0 hours) to obtain an off-white solid, compound of formula:

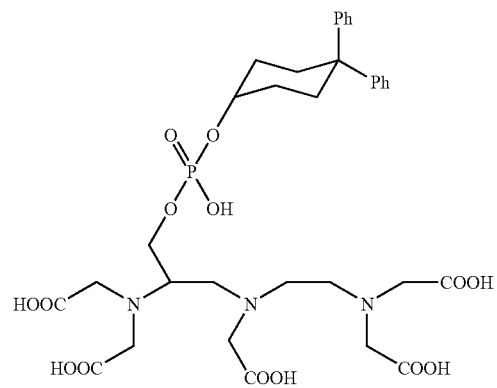

(65.5 g, Yield: 68.89% Purity: 99.45% by weight, 98.95% by area, 3.02% water and 97.81% chelatables).

EXPERIMENTAL

Three types of samples were prepared and evaluated. The first was a control sample containing human serum albumin (HSA) without a contrast agent. The other two samples contained HSA and the non-specific agent Gd-DTPA and the HSA-specific agent MS-325, respectively.

In these examples, the longitudinal relaxivities ($R_1$, $mM^{-1}$ $sec^{-1}$) were monitored and obtained at 20 MHz by determining the relaxation rate ($1/T_1$) of water protons in phosphate buffered saline (PBS, 150 mM NaCl, 10 mM phosphate, pH=7.4), in PBS solutions containing 4.5 wt % HSA, or in gels containing 4.5 wt % HSA and 1% Agar. The dependence of temperature on relaxivity ($R_1$) was observed by varying the temperature of the samples with a circulating water bath and monitoring sample temperature with a thermocouple.

Example 1

Monitoring the Thermal Necrosis of 4.5% HSA

The following three samples were prepared in solutions of 4.5% HSA: (1) a control sample without a contrast agent; (2) a comparative sample with Gd-DTPA; and (3) a sample with MS-325. The samples with Gd-DTPA and MS-325 were prepared by adding an aqueous formulation (pH=7) comprising either Gd-DTPA or MS-325 to the 4.5% HSA solution. The resulting mixtures had a concentration of 0.3 mM Gd-DTPA and 0.1 mM MS-325, respectively.

The three samples were then used to monitor the thermal denaturation of the 4.5% HSA solutions. To do this, $T_1$ data (and thus $R_1$ data ($=1/T_1$)) for each sample was collected at 20 MHz over a temperature range of 20–60° C. Each sample was then removed from the NMR and heated at 85° C. for 15 minutes to induce thermal denaturation of the HSA. Subsequently, the sample was returned to the NMR and $T_1$ data was collected at this higher temperature. See Table 1 below.

TABLE 1

| Temperature (° C.) | $R_1$ 4.5% HSA | $R_1$ Gd-DTPA | $R_1$ MS-325 |
|---|---|---|---|
| 7.3 | 0.396 | 9.4556 | 31.2 |
| 11.7 | 0.319 | 8.8125 | 33.4 |
| 16.2 | 0.246 | 8.0690 | 36.0 |

TABLE 1-continued

| Temperature (° C.) | $R_1$ 4.5% HSA | $R_1$ Gd-DTPA | $R_1$ MS-325 |
|---|---|---|---|
| 20.6 | 0.181 | 7.4182 | 38.6 |
| 25.0 | 0.123 | 6.7426 | 40.6 |
| 29.5 | 0.072 | 6.2117 | 42.0 |
| 33.9 | 0.033 | 5.7089 | 42.8 |
| 38.4 | 0.000 | 5.2984 | 42.4 |
| 42.8 | −0.026 | 4.8917 | 42.3 |
| 47.3 | −0.041 | 4.5992 | 41.3 |
| 51.7 | −0.045 | 4.3083 | 39.5 |
| 56.2 | −0.056 | 4.0592 | 37.5 |
| 60.6 | −0.065 | 3.8806 | 33.3 |
| 85.0 | 0.084 | 4.2102 | 10.8 |

As Table 1 shows, after thermal denaturation of the three HSA-containing solutions, the sample that also contained the HSA-specific contrast agent MS-325 demonstrated a significant decrease in the observed $R_1$ (a loss of 26.7 mM$^{-1}$ sec$^{-1}$) during denaturation of the HSA as measured from immediately before denaturation (56.2° C.) to immediately after denaturation (85° C.). However, the sample that contained the non-specific contrast agent Gd-DTPA, even at a concentration of three times that used for the MS-325 sample, showed little change in $R_1$ (a loss of only 0.1 mM$^{-1}$ sec$^{-1}$) during denaturation. This indicates that Gd-DTPA does not bind to either native or denatured HSA.

After the above data was obtained, the denatured samples were allowed to cool to physiological temperature (37° C.) and $T_1$ data was again collected. The sample with MS-325 maintained a significant loss in $R_1$ (a net loss of 25 mM$^{-1}$ sec$^{-1}$) while the sample with Gd-DTPA demonstrated only small changes in $R_1$ (a net loss of 0.5 mM$^{-1}$ sec$^{-1}$)

Example 2

MRI Imaging of the Thermal Denaturation of HSA at 1.0 Tesla

The following samples were prepared in 1% agar gels containing 4.5% HSA: (1) a control sample without a contrast agent; (2) a comparative sample with Gd-DTPA; and (3) a sample with MS-325. The contrast agents were added in an amount sufficient such that the concentration of Gd-DTPA and MS-325 were 0.3 mM Gd-DTPA and 0.1 mM MS-325, respectively. Such agar gels containing 4.5% HSA are referred to as "phantoms".

Initial $T_1$-weighted MRI scans (FISP-3D, TR=15, TE=4, alpha=30) at 1.0 Tesla of the agar phantoms were then obtained at a temperature of about 25° C. The initial scans revealed that the phantoms containing MS-325 were brighter than the phantoms containing Gd-DTPA (comparative sample) or 4.5% HSA alone (control sample); this result was as expected due to the specific binding of MS-325 to HSA.

The phantoms were then heated in a circulating water bath with additional $T_1$-weighted MRI scans obtained over time. As the temperature increased, the phantoms containing MS-325 remained much brighter (less signal intensity loss as measured in % ROI (region of interest)) than the phantoms containing Gd-DTPA or 4.5% HSA alone. See Table 2 below.

TABLE 2

| Time (Min.) | Temperature (° C.) | % Loss ROI, 4.5% HSA | % Loss ROI, 0.3 mM Gd-DTPA in 4.5% HSA | % Loss ROI, 0.1 mM MS-325 in 4.5% HSA |
|---|---|---|---|---|
| 0 | 25.3 | −0.41519 | −0.24557 | 0.0000 |
| 10 | 29.6 | −4.2635 | −5.1875 | −4.4755 |
| 20 | 38.3 | −6.8972 | −12.806 | −6.4144 |
| 30 | 45.0 | −10.360 | −18.985 | −11.241 |
| 40 | 53.0 | −15.205 | −30.964 | −26.153 |
| 50 | 64.7 | −20.250 | −43.833 | −49.262 |
| 60 | 72.8 | −20.667 | −46.086 | −69.499 |
| 70 | 87.1 | −20.953 | −47.529 | −76.469 |
| 120 | 35.5 | −4.9098 | −10.190 | −31.869 |

As the phantoms were heated above 50–60° C., they became opaque in color, corresponding to the thermal denaturation of the HSA. At the same time, as Table 2 shows, a dramatic loss of signal intensity was observed for the phantoms that contained MS-325 (76% loss in intensity). However, the phantoms that contained Gd-DTPA or HSA alone, produced only a modest change in signal intensity. The Gd-DTPA phantoms, even at a Gd-DTPA concentration that was three times that used for the MS-325 phantoms remained as constant dark images during the MRI scans after thermal denaturation.

After the above data was collected, the denatured were then allowed to cool to normal physiologic re (37° C.). The phantoms containing MS-325 d their loss in signal intensity (32% loss). The phantoms and the phantoms containing Gd-DTPA showed still showed only a 5% and 10% decrease in signal intensity, respectively, after denaturation.

According to these results, the contrast agents useful in the method of this invention can provide a very sensitive indication of the thermal denaturation of HSA. Indeed, even when three times the concentration of another contrast agent was used, this higher concentration could not provide the sensitivity required to monitor HSA's thermal denaturation.

Example 3

Ethanol Denaturation of HSA

The following three samples were prepared in solutions of 4.5% HSA: (1) a control sample without a contrast agent; (2) a comparative sample with Gd-DTPA; and (3) a sample with MS-325. The samples with Gd-DTPA and MS-325 were prepared by adding an aqueous formulation (pH=7) comprising either Gd-DTPA or MS-325 to the 4.5% HSA solution. The resulting mixtures had a concentration of 0.31 mM Gd-DTPA and 0.08 mM MS-325, respectively.

Absolute ethanol was then titrated to each of the samples. $T_1$ data (and thus $R_1$ data ($=1/T_1$)) was collected at 20 MHz and 37° C. after each addition of ethanol. See Table 3 below.

TABLE 3

| Ethanol (%) | $R_1$ 4.5% HSA | Ethanol (%) for Gd-DTPA | $R_1$ 0.31 mM Gd-DTPA | Ethanol (%) for MS-325 | $R_1$ 0.08 mM MS-325 |
|---|---|---|---|---|---|
| 0.0000 | −0.000 | 0.0 | 4.1737 | 0.0 | 42.216 |
| 8.7382 | 0.030 | 16.1 | 4.7191 | 0.9 | 40.848 |
| 16.072 | 0.060 | 27.8 | 5.0021 | 1.9 | 39.541 |
| 22.315 | 0.090 | 36.6 | 4.9347 | 2.8 | 38.423 |
| 27.693 | 0.109 | 43.5 | 4.7997 | 3.7 | 37.064 |
| 32.375 | 0.125 | 49.0 | 4.4623 | 4.5 | 36.375 |
| 36.487 | 0.128 | | | 5.4 | 35.234 |

TABLE 3-continued

| Ethanol (%) | $R_1$ 4.5% HSA | Ethanol (%) for Gd-DTPA | $R_1$ 0.31 mM Gd-DTPA | Ethanol (%) for MS-325 | $R_1$ 0.08 mM MS-325 |
|---|---|---|---|---|---|
| 40.128 | 0.142 | | | 6.2 | 34.576 |
| 43.375 | 0.153 | | | 7.1 | 33.895 |
| 46.287 | 0.168 | | | 7.9 | 33.099 |
| | | | | 8.7 | 32.224 |
| | | | | 10.2 | 31.689 |
| | | | | 11.7 | 30.403 |
| | | | | 16.4 | 26.939 |
| | | | | 22.8 | 21.456 |
| | | | | 28.3 | 17.428 |
| | | | | 33.1 | 14.082 |
| | | | | 37.3 | 11.187 |
| | | | | 41.0 | 9.6943 |
| | | | | 44.2 | 8.9506 |
| | | | | 47.2 | 8.7970 |

As Table 3 demonstrates, during ethanol ablation of the 4.5% HSA solutions, the sample containing MS-325 showed a significant decrease in the observed relaxivity (33 mM$^{-1}$ sec$^{-1}$) and thus, allowing for the detection of ethanol induced necrosis. However, the sample containing Gd-DTPA (even at almost four times the concentration of MS-325) showed only a minor change in observed relaxivity (0.3 mM$^{-1}$ sec$^{-1}$).

We claim:

1. A method for monitoring treatment of a tissue comprising HSA for evaluating efficacy of interventional therapy in a patient, said method comprising:
   a) administering a contrast agent to said patient, wherein said contrast agent is selected from the group consisting of MS-315, MS-317, MS-322, MS-323, MS-325, MS-326, MS-327, and MS-328;
   b) subjecting said patient to magnetic resonance imaging to determine an initial signal intensity value in a region of interest of said undesired tissue;
   c) applying an interventional therapy to at least a portion of said undesired tissue in order to treat said undesired tissue; and
   d) monitoring with magnetic resonance imaging a change in said initial signal intensity value in said region of interest of said undesired tissue.

2. The method of claim 1, wherein said tissue is selected from the group consisting of cancerous tissue, tumorous tissue, and neoplastic tissue.

3. The method of claim 2, wherein said tissue is cancerous tissue.

4. The method of claim 1, wherein said interventional therapy is selected from the group consisting of a thermal energy generation, a cryoablation, an injection of a denaturing liquid, an injection of a chemotherapeutic agent, and a photodynamic therapy.

5. The method of claim 4, wherein said interventional therapy is said generation of thermal energy, and wherein said thermal energy is generated by a source selected from the group consisting of one or more focused ultrasound waves, radiofrequency waves, microwaves, and lasers.

6. The method of claim 1, further comprising: e) stopping said interventional therapy application when said change in said initial signal intensity value in said region of interest of said undesired tissue is more than about a 10% reduction in said initial signal intensity value.

* * * * *